United States Patent [19]
Jauregui et al.

[11] Patent Number: 6,017,760
[45] Date of Patent: Jan. 25, 2000

[54] ISOLATION AND CULTURE OF PORCINE HEPATOCYTES

[75] Inventors: Hugo O. Jauregui, Providence; Sharda Naik, Cranston; Henry Santangini, Cranston; Donna M. Trenkler, Greene, all of R.I.

[73] Assignee: Rhode Island Hospital, Providence, R.I.

[21] Appl. No.: 08/541,462

[22] Filed: Oct. 10, 1995

[51] Int. Cl.$^7$ .............................. C12N 5/00; C12N 5/06; C12N 11/00; C12N 11/04

[52] U.S. Cl. .................... 435/378; 435/325; 435/379; 435/384; 435/389; 435/394; 435/395; 435/399; 435/400; 435/401; 435/402; 435/174; 435/29; 435/1.1

[58] Field of Search ................... 435/240, 240.2, 435/240.31, 240.242, 240.241, 240.243, 240.23, 1.1, 29, 174, 325, 378, 379, 384, 389, 394, 395, 399, 400, 401, 402

[56] References Cited

U.S. PATENT DOCUMENTS

| | | | |
|---|---|---|---|
| 4,352,887 | 10/1982 | Reid et al. ............................. | 435/240 |
| 4,994,388 | 2/1991 | Hillegas et al. .................. | 435/240.243 |
| 4,996,154 | 2/1991 | Gabriels, Jr. ...................... | 435/240.241 |
| 5,043,260 | 8/1991 | Jauregui .................................. | 435/1 |
| 5,122,470 | 6/1992 | Banes ............................... | 435/240.241 |
| 5,153,133 | 10/1992 | Schwarz et al. .................... | 435/240.24 |
| 5,162,225 | 11/1992 | Sager et al. ....................... | 435/240.243 |
| 5,175,092 | 12/1992 | Gabriels, Jr. .............................. | 435/29 |
| 5,264,359 | 11/1993 | Enami et al. .................... | 4535/240.23 |
| 5,270,192 | 12/1993 | Li et al. .................................. | 435/174 |

OTHER PUBLICATIONS

Waxman et al. 1990 Biochemical Journal 271 113–119, Jan. 1990.

Quistorff 1985 Biochem J 229 221–6, Jan. 1, 1985.

Alpini et al., Recent Advances in the Isolation of Liver Cells, Hepatology 20:494–514, 1994.

Arterburn et al., A Morphological Study of Differentiated Hepatocytes In Vitro, Hepatology 22:175–187, 1995.

Basile et al., The Pathogenesis and Treatment of Hepatic Encephalopathy: Evidence for the Involvement of Benzodiazepine Receptor Ligands, Pharmacol. Rev. 43:27–71, 1991.

Basile et al., Brain Concentrations of Benzodiazepines are Elevated in an Animal Model of Hepatic Encephalopath, Proc. Natl. Acad. Sci. USA 87:5263–5267, 1990.

Bryson, Acetaminophen, Ch. 35 in Comprehensive Review in Toxicology, 2nd ed, Aspen Publishers, 1989, pp. 415–422.

Butterworth et al., Ammonia: Key Factor in the Pathogenesis of Hepatic Encephalopathy, Neurochemical Pathology 6:1–12, 1987.

Clayton et al., Liver–Specific RNA Metabolism in Hepatoma Cells: Variations in Transcription Rates and MRNA Levels, Molecular and Cellular Biology 5:2633–2641, 1985.

Colin and Sirois, Simultaneous Determination of the Major Metabolites of Styrene and Acetaminophen, and of Unchanged Acetaminophen . . . Chromatography, Journal of Chromatography 377:243–251, 1986.

Demetriou et al., New Method of Hepatocyte Transplantation and Extracorporeal Liver Support, Ann Surg. 204:259–271, 1986.

Dicker et al., Increased Catalytic Activity of Cytochrome P–450IIE1 in Pericentral Hepatocytes Compared to Periportal Hepatocytes . . . Rats, Biochimica et Biophysica Acta 1073:316–323, 1991.

Dixit et al., Hepatocyte Immobilization on Phema Microcarriers and Its Biologically Modified Forms, Cell Transplantation 1:391–399, 1992.

Enat et al., Hepatocyte Proliferation In Vitro: Its Dependence on the Use of Serum–Free Hormonally Defined Medium and Substrata of Extracellular Matrix, PNAS USA 81:1411–1415, 1984.

Fujioka et al., Carboxyfluorescein (CFSE) Labelling of Hepatocytes for Short–Term Localization Following Intraportal Transplantation, Cell Transplantation 3:397–408, 1994.

Gebhardt, Metabolic Zonation of the Liver: Regulation and Implications for Liver Function, Pharmac. Ther. 53:275–354, 1992.

Gebhardt et al., Different Drug Metabolizing Capapcities in Cultued Periportal and Pericentral Hepatocytes, Biochemical Pharmacology 48:761–766, 1994.

Gerlach et al., Nonenzymatic Versus Enzymatic Hepatocyte Isolation From Pig Livers for Larger Scale. . . Liver Cell Perfusion Systems, The International Journal of Artificial Organs 16:677–681, 1993.

Gerlach et al., Comparison of Four Methods for Mass Hepatocyte Isolation from Pig and Human Livers Transplantation 57:1318–1322, 1994.

Gerlach et al., Hepatocyte Culture Between Woven Capillary Networks: A Microscopy Study, Artificial Organs 18:226–230, 1994.

Gupta et al., Hepatocyte Transplantation: An Alternative System for Evaluating Cell Survival and Immunoisolation, The International Journal of Artificial Organs 16:155–163, 1993.

Hager et al., Neonatal Hepatocyte Culture on Artificial Capillaries, Assaio Journal 6:26–35, 1983.

Hayner et al., Ponceau S.: A Sensitive Method for Protein Determination in Freshly Isolated and Cultured Cells Journal of Tissue Culture Methods 7:77–80, 1982.

(List continued on next page.)

*Primary Examiner*—Lynette F. Smith
*Assistant Examiner*—Mary K Zeman
*Attorney, Agent, or Firm*—Fish & Richardson P.C.

[57] ABSTRACT

A perfusion device such as a liver assist device containing a housing defining a perfusion inlet and a perfusion outlet, a porous membrane structure mounted within said housing to define a perfusion compartment and an adjacent hepatocyte compartment, and porcine hepatocytes isolated from a porcine liver by retrograde perfusion.

26 Claims, 16 Drawing Sheets

OTHER PUBLICATIONS

Ho et al., Determination of Nitrazepam and Temazepam in Plasma by High–Performance Liquid Chromatography, Therapeutic Drug Monitoring 5:303–307, 1983.

Isom et al., Maintenance of Differentiated Rat Hepatocytes in Primary Culture, PNAS USA 82:3252–3256, 1985.

Jauregui and Sharda, Diazepam Metabolic Activity in Long Term Monolayer Cultures of Rat, Rabbit, and Piglet Hepatocytes, Abstract, Artificial Organs 15:295, 1991.

Jauregui et al., Xenobiotic Induction of P–450 PB–4 (IIB1) and P–450C (IA1) and Associated Monooxygenase Activities in Primary Cultures of Adult Rat Hepatocytes, Xenobiotica 21:1091–1106, 1991.

Jauregui et al., Trypan Blue Dye Uptake and Lactate Dehydrogenase in Adult Rat Hepatocytes—Freshly Isolated Cells . . . Monolayer Cultures, In Vitro 17:1100–1110, 1981.

Jauregui et al., Diazepam Metabolism in Perfused Cultures of Adult Rat Hepatocytes, In Hepatic Encephalopathy Butterworth & Layrargues (eds.), Humana Press, Clifton NJ, 1989, pp. 339–351.

Jauregui et al., P–450 Activity in Monolayer Cultures of Hepatocytes Seeded in Polystyrene Tissue Culture Dishes, Trans. Am. Soc. Artif. Intern. Organs, vol. XXXII, 357–359, 1986.

Jauregui et al., Trypan Blue Dye Uptake and Lactate Dehydrogenase in Adult Rat Hepatocytes—Freshly Isolated Cells, Cell Suspensioins, and Primary Monolayer Cultures, In Vitro 17:1100–1110, 1981.

Jauregui et al., In Vivo Evaluation of a Hollow Fiber Liver Assist Device, Hapatology 21:460–469, 1995.

Jauregui et al., Adult Rat Hepatocyte Cultures as the Cellular Component of an Artificial Hybrid Liver, In Biomaterials in Artificial Organs, Paul et al. (eds.), Macmillan Press, 1983, pp. 130–140.

Jauregui et al., Attachment and Long Term Survival of Adult Rat Hepatocytes in Primary Monolayer Cultures: Comparison of . . . Media Formulations, In Vitro Cellular & Developmental Biology 22:13–22 1986.

Jenkins et al., The Role of Transplantation in Liver Disease, Surgical Clinics of North America 69:371–382 1989.

Jones et al., Fulminant Hepatic Failure, Ch. 17 in Manifestations of Abnormal Liver Function, pp. 460–492.

Kasai et al., Cellulose Microcarrier for High–Density Culture of Hepatocytes, Transpslantation Proceedings 24:2933–2934, 1992.

Kay, Hepatocyte Transplantation for Liver Gene Therapy, Cell Transplantation 2:405–406, 1993.

Kelly et al., Modulation of the Liver Specific Phenotype in the Human Hepatoblastoma Line HEP G2, In Vitro Cellular & Developmental Biology 25:217–222, 1989.

Kobayashi et al., Enhanced Adhesion and Survival Efficiency of Liver Cells in Culture Dishes Coated with a Lactose–Carrying Styrene Homopolymer, Makromol. Chem., Rapid Commun. 7:645–650, 1986.

Koide et al., Formation of Multicellular Spheroids Composed of Adult Rat Hepatocytes in Dishes with Positively Charged Surfaces . . . Nonadherent Environments, Experimental Cell Research 187:227–235, 1990.

Macklis et al., Cross–Linked Collagen Surface for Cell Culture That is Stable, Uniform, and Optically Superior to Conventional Surfaces, In Vitro Cellular & Developmental Biology 21:189–194, 1985.

Michalopoulos et al., Control of Hepatocyte Replication by Two Serum Factors, Cancer Research 44:4414–4419, 1984.

Mito and Kusano, Hepatocyte Transplantation in Man, Cell Transplantation 2:65–74, 1993.

Morsiani et al., Automated Large–Scale Production of Porcine Hepatocytes for Bioartificial Liver Support, Transplantation Proceedings 26:3505–3506, 1994.

Muller and Jauregui, Letters to the Editor, Artificial Organs 18:44–45, 1993.

Munoz et al., Liver Transpslantation, Medical Clinics of North America 73:1011–1039, 1989.

Naik et al., Cell Transplantation, Influence of Different Substrates in Detoxification Activity of Adult Rat Hepatocityes in Long–Term Culture: Implications for Transplantation, 1:61–69, 1992.

Peleman et al., Orthotopic Liver Transplantation for Acute and Subacute Hepatic Failure in Adults, Hepatology 7:484–489, 1987.

Ponder et al., Mouse Hepatocytes Migrate to Liver Parenchyma and Function Indefinitely After Intrasplenic Transplantation, Proc. Natl. Acad. Sci. USA 88:1217–1221, 1991.

Reid et al., Culturing Hepatocytes and Other Differentiated Cells, Hepatology 4:548–559, 1984.

Rozga et al., A Bioartificial Liver to Treat Severe Acute Liver Failure, Annals of Surgery 219:538–546, 1994.

Rozga et al., Control of Cerebral Oedema by Total Hepatectomy and Extracorporeal Liver Support in Fulminant Hepatic Failure, The Lancet 342:898–899, 1993.

Rozga et al., Development of a Hybrid Bioartificial Liver, Annals of Surgery 217:502–511, 1993.

Rozga et al., Development of a Bioartificial Liver: Properties and Function of a Hollow–Fiber Module Inoculated with Liver Cells, Hepatology 17:258–265, 1993.

Schrode et al., Induction of Glutamine Synthetase in Periportal Hepatocytes by Cocultivation with a Liver Epithelial Cell Line, European Journal of Cell Biology 53:35–41, 1990.

Seglen, Preparation of Isolated Rat Liver Cells, Methods in Cell Bio. 13:29–81, 1976.

Sussman et al., Reversal of Fulminant Hepatic Failure Using an Extracorporeal Liver Assist Device, Hepatology 16:60–65, 1992.

Sussman and Kelly, Improved Liver Function Following Treatment with an Extracorporeal Liver Assist Device, Artif. Organs. 17:27–30, 1993.

Sussman et al., Letters to the Editor, Artificial Organs 17:43–44, 1993.

Taylor, Receptors for Insulin and Insulinlike Growth Factors, In The Liver: Biology and Pathobiology Arias et al. (eds.), Raven Press, NY, 1988, pp. 753–767.

Wolf et al., Trans. Amer. Soc. Artif. Int. Organs 21:16–26, 1975.

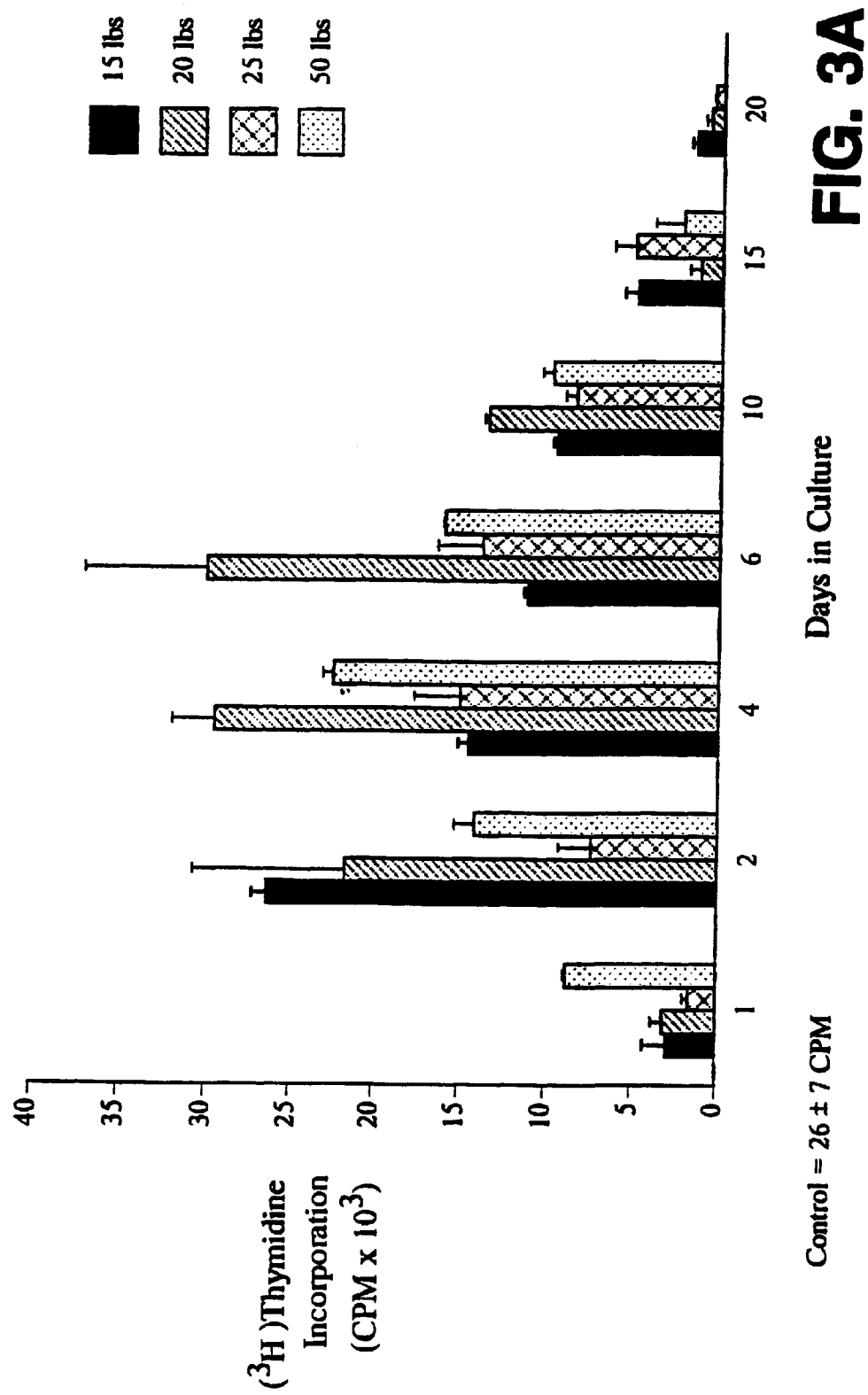

ISOLATION AND CULTURE OF PORCINE HEPATOCYTES

BACKGROUND OF THE INVENTION

The invention relates to isolation and culture of porcine hepatocytes, useful, e.g., in liver assist devices.

The primary requirement of cells in a liver support system, e.g., a liver assist device (LAD), is the preservation of the in vivo metabolic functions that prevent and/or decrease the progress of hepatic encephalopathy (HE) in patients with acute liver failure. While the precise pathogenesis of this syndrome remains unknown, endogenous benzodiazepine-like substances (Basile et al., 1991, Pharmacol. Rev. 43:27–71) and ammonia (Butterworth et al., 1987, Neurochemical Pathology 6:1–12) have both been identified as important factors in its development. Benzodiazepines, as well as other drugs or toxins, are metabolized by the liver by a family of enzymes that catalyze their oxidative degradation (phase I metabolism), which, in turn, facilitates further detoxification steps (phase II metabolism). The oxidative enzymes, known collectively as the P450 system, can decay very rapidly in cultured hepatocytes (Reid et al., 1984, Hepatology 4:548–559) and are partially or poorly expressed in liver cell lines (Clayton et al., 1985, Mol. Cell. Biol. 5:2633–2641). Cultured hepatocytes have also been reported to lose function and ultimately die over the first few days in culture (Reid et al., supra).

Since healthy human liver cells are seldom available in adequate numbers to support clinical LAD use, hepatoma cells (malignant and transformed hepatocytes) (Wolf et al., 1975, Trans. Amer. Soc. Artif. Int. Organs 21:16–26), have been used to seed the intercapillary space of hollow fiber bioreactors. Mouse liver cells (Hager et al., 1983, ASAIO 6:26–35) and rat hepatocytes (Jauregui et al., 1989, In Butterworth et al., eds., Hepatic Encephalopthy, New Jersey: The Humana Press, pp. 339–351) have also been used to seed LAD devices. While rodent hepatocytes offer a model for preliminary LAD research, the limited number of liver cells available per animal prohibits a direct scale up to human devices. Primary porcine hepatocytes (Rozga et al., 1993, Ann. Surg. 217:502–511; Rozga et al., 1994, Ann. Surg. 219:538–546) have recently been used in LADs; however primary hepatocytes are difficult to proliferate in vitro (Enat et al., 1984, Proc. Natl. Acad. Sci. U.S.A. 81:1411–1415) and lose phenotypic expression in culture (Reid et al., supra).

SUMMARY OF THE INVENTION

The inventors have discovered a method of isolating a population of primary porcine hepatocytes enriched for pericentral cells which are high in P450 enzymes required for the metabolism of toxic compounds (e.g., drugs and endogenous metabolites) and have devised methods of culturing such cells to prolong their proliferative and enzymatic activity in vitro. Primary porcine hepatocytes isolated and cultured according to the invention represent significant advantages over transformed cell lines and conventional isolates of primary cells.

Accordingly, the invention features a perfusion device containing a sample of porcine hepatocytes isolated by retrograde perfusion of a porcine liver. Preferably, at least 9% of the hepatocytes are pericentral cells; more preferably, at least 10% of the hepatocytes are pericentral cells; and most preferably, at least 20% of the hepatocytes are pericentral cells. Pericentral cells are hepatocytes which surround the central vein of the liver and which stain positively for the marker enzyme, glutamine synthetase. These cells are also referred to as perivenous or acinar zone 3 hepatocytes. The sample of hepatocytes is further characterized by enhanced P450 enzyme activity, e.g., 7-ethoxycoumarin (7-EC) metabolism of at least 0.25 µg/ml hydroxycoumarin per hour; enhanced glucuronidation enzyme activity, e.g., acetaminophen metabolism of at least 10 µg/ml acetaminophen glucuronide per hour, or diazapem metabolism of at least 3 µg/ml total diazepam metabolites per hour; and/or enhanced $NH_3$ metabolizing enzyme activity, e.g., $NH_3$ metabolism of 45 µg/ml of $NH_3$ per hour (or at least 40% of the $NH_3$ present in the media at the beginning of the culture is metabolized by the porcine hepatocytes). For example, the hepatocytes in the perfusion device preferably have the following functional parameters: diazepam metabolic activity of at least 8 µg/ml total diazepam metabolites per hour; 7-EC metabolic activity of at least 1.5 µg/ml 7-hydroxycoumarin per hour; acetaminophen metabolic activity of at least 25 µg/ml acetaminophen glucuronide per hour; $NH_3$ metabolism of at least 60 µg/ml of $NH_3$ per hour (or at least 70% of the $NH_3$ present in the media at the beginning of the culture is metabolized by the porcine hepatocytes); and/or proliferative activity for at least 24 hours of in vitro culture, i.e., post-isolation. Preferably, the proliferative activity of the hepatocytes can be detected for at least 3 days, more preferably for at least 4 days, more preferably for at least 6 days, and most preferably for at least 10 days of in vitro culture.

Diazepam metabolic activity may be evaluated as follows: $4 \times 10^6$ cells are cultured in 5 mls of medium containing 50 µg/ml diazepam (250 µg of diazepam), and the amount of diazepam metabolites present in the culture supernatant is measured after 3 hours of culture. 7-EC metabolism may be evaluated as follows: $4 \times 10^6$ cells are cultured in 5 mls of medium containing 50 µg/ml 7-EC (250 µg of 7-EC), and the amount of 7-hydroxycoumarin present in the culture supernatant is measured after 3 hours of culture. Acetaminophen metabolism may be evaluated as follows: $4 \times 10^6$ cells are cultured in 5 mls of medium containing 5 mM acetaminophen (0.75 mg/ml; 3.75 g of acetaminophen), and the amount of acetaminophen glucuronide present in the culture supernatant is measured after 3 hours of culture. Ammonia metabolism may be evaluated as follows: $4 \times 10^6$ cells are cultured in 5 mls of medium containing 1.5 mM $NH_3$ (0.08 mg/ml $NH_4Cl$), and the amount of $NH_3$ present in the culture supernatant is measured after 3 hours of culture.

A method of manufacturing a perfusion device is also within the invention. A perfusion device is made by providing a housing defining a perfusion inlet and a perfusion outlet; providing a porous membrane structure mounted within the housing to define a perfusion compartment or compartments and an adjacent hepatocyte compartment; and seeding the hepatocyte compartment with isolated primary porcine hepatocytes, at least 9% of which are pericentral cells. The membrane structure can be provided by hollow fibers, in which case the perfusion compartments are the flow passage within the fibers and the hepatocyte compartment is provided by the space between the fibers. The hepatocytes can be immobilized on hollow fibers or another solid or semi-solid support in the hepatocyte compartment. The fibers or other support may be coated with a substance, e.g., collagen, lectin, laminin, or fibronectin, to facilitate attachment of the hepatocytes. Alternatively, the hepatocytes in the hepatocyte compartment may be seeded onto particles, e.g., solid or semi-porous microcarrier particles, and cultured in the hepatocyte compartment.

The invention also features an isolated sample of primary porcine hepatocytes at least 9% of which are pericentral cells. Preferably, the sample contains at least 10% pericentral cells. The isolated sample of hepatocytes can further be defined by the detection one or more of the following spectrum of functional activities: diazepam metabolic activity of at least 3 µg/ml total diazepam metabolites per hour; 7-EC metabolic activity of at least 0.25 µg/ml 7-hydroxycoumarin per hour; acetaminophen metabolic activity of at least 10 µg/ml acetaminophen glucuronide per hour; $NH_3$ metabolism of at least 60 µg/ml of $NH_3$ per hour (or at least 70% of the $NH_3$ present in the media at the beginning of the culture is metabolized by the porcine hepatocytes); proliferative activity for at least 24 hours of in vitro culture. Preferably, the proliferative activity of the hepatocytes can be detected for at least 3 days, more preferably for at least 4 days, more preferably for at least 6 days, and most preferably for at least 10 days of in vitro culture.

In another aspect, the invention includes a method of isolating a sample of primary porcine hepatocytes enriched for pericentral cells. This method has been adapted to optimize the yield of highly metabolically-active cells, i.e., pericentral cells, and includes the following steps: providing a pig, preferably a live pig; perfusing the porcine liver in a retrograde manner with a solution to disrupt the cellular integrity of the liver, e.g., a buffered collagenase solution; removing the porcine liver from the pig; and separating the hepatocytes from cellular debris and other liver constituents, e.g, non-parenchymal cells, to yield a sample of hepatocytes containing at least 9% pericentral cells and preferably at least 10% pericentral cells. By "retrograde perfusion" is meant administration of a flow of a solution contrary to the physiologic direction of blood flow. For example, according to the invention, retrograde perfusion of a porcine liver is carried out by introducing a perfusion buffer through the vena cava. Retrograde perfusion of the liver may be carried out in vitro or in situ. Preferably, the pig from which the liver is extracted is at least 15 pounds in weight, more preferably between 20–35 pounds in weight. The pig is preferably at least 6 weeks old and is most preferably between 6 and 8 weeks old.

The viability, proliferative activity, and metabolic activity of porcine hepatocytes isolated according to the invention may be further enhanced by optimizing the culture conditions of the hepatocytes prior to seeding the hepatocytes into the perfusion device. By "metabolically active" or "enzymatically active" is meant able to process a potentially toxic compound, e.g., a drug or endogenous metabolite, into a less toxic or non-toxic compound. The claimed method of enhancing the viability and metabolic activity of primary porcine hepatocytes in vitro includes the following steps: providing a sample of porcine hepatocytes, preferably isolated as described above; contacting the sample with a suspension of particles, e.g, microcarriers, thereby allowing the hepatocytes to attach to the particles; and culturing the particles in a roller bottle. Hepatocytes cultured as described typically form cell-microcarrier aggregates. Cells cultured in this manner proliferate for at least 24 hours of in vitro culture and are at least 2 times more metabolically active compared to a sample of porcine hepatocytes cultured in a conventional manner, e.g., grown in a cellular monolayer of a tissue culture vessel. Preferably, hepatocyte proliferation can be detected for at least 3 days, more preferably at least 6 days, and most preferably at least 10 days of in vitro culture and the hepatocytes can process at least 5 times, more preferably at least 10 times, and most preferably at least 20 times, as much of a toxic compound, e.g., diazepam, compared to porcine hepatocytes grown in a monolayer culture.

In addition to the physical conditions of the culture method, the composition of the culture medium was also found to affect the proliferative and metabolic activity of the hepatocyte sample. The cell-microcarrier aggregates are preferably cultured in a medium comprising at least 1% fetal bovine serum (FBS); more preferably the medium contains 2% fetal bovine serum; more preferably 5% FBS. Most preferably, the culture medium contains 10% FBS and between 50–100 ng/ml insulin.

The ability of hepatocytes to detoxify a compound can also be enhanced by culturing isolated hepatocytes in medium containing dimethyl sulfoxide (DMSO), e.g., 5% FBS+2% DMSO or 2% FBS+2% DMSO. Alternatively, FBS may be omitted from the culture medium altogether, and the hepatocytes cultured in a serum-free culture media. For example, hepatocytes may be cultured in a standard culture media supplemented with insulin, transferrin, and/or selenium, together with 2% DMSO.

The invention also provides a method of neutralizing a toxin, e.g., an endogenous compound such as a metabolite or an exogenously-administered compound such as a drug, in a human bodily fluid which includes the steps of contacting the bodily fluid, e.g., blood or plasma, with a sample of hepatocytes isolated and cultured as described above. The toxins in the fluid are efficiently processed by the highly metabolically-active hepatocytes, and thus, the fluid is rendered non-toxic. The processed bodily fluid may then be returned to the patient from which it was derived. For example, the following toxins may be present in bodily fluid taken from a patient and neutralized according to the invention: benzodiazepine, ammonia, 7-EC, lidocaine, and acetaminophen. Contact of the patient-derived bodily fluid with the isolated sample may take place in any device capable of providing adequate contact of isolated hepatocytes with a bodily fluid, such as a perfusion device, e.g., a LAD or bioreactor.

Porcine hepatocytes isolated and cultured according to the invention can be transferred to any type of perfusion device for use as the biological component thereof. The diversity of hepatic function maintained by cultured porcine hepatocytes for 10 days or more in culture is an important advantage of the perfusion devices of the invention. The methods of the invention optimize the isolation of hepatocytes with high metabolic activity and yield a population of cells more suitable for use in an LAD than other methods of isolation. The isolation method of the invention preferentially targets the liver lobule pericentral cells, thereby permitting retrieval of a sample of hepatocytes which is free of other cellular constituents of the porcine liver, e.g., Kupffer cells or other nonparenchymal cells. Presence of such non-hepatocyte cells in LADs increases the possibility of adverse immune responses in patients after the bodily fluids which have been processed by the perfusion device are returned to the patient. To ensure the proper distribution of cell types, the composition of the isolated sample of primary porcine hepatocytes is assessed by immunohistochemical staining and functional assays to determine enzymatic activity.

An advantage of the culture methods of the invention is that hepatocytes attached onto particles, e.g., solid or semi-porous particles, and cultured using roller bottles, have greater detoxification activity than freshly isolated cells or cells cultured by other methods. Therefore, when hepatocytes are cultured according to the invention, fewer hepatocytes (and therefore, fewer donor animals) are required per perfusion device to perform the same function compared to freshly isolated cells or cells cultured by other methods.

Another advantage of the invention is that proliferating hepatocytes cultured as described above maintain a differentiated phenotype, e.g., detoxification function such as P450 enzymatic activity, for several days of in vitro culture.

In addition, the increased capacity of hepatocytes to proliferate when cultured according to the invention reduces the cost of making and operating perfusion devices, e.g., LADs. The enhanced proliferative activity also allows ample time for quality control testing to be performed on the cells and/or perfusion devices containing the cells prior to distribution to patient treatment centers.

Other features and advantages of the invention will be apparent from the following description of the preferred embodiments thereof, and from the claims.

BRIEF DESCRIPTION OF THE DRAWINGS

FIG. 3A is a bar graph showing $^3$H-thymidine incorporation by porcine hepatocyte isolated from pigs of various weights cultured in roller bottles.

DESCRIPTION OF THE PREFERRED EMBODIMENTS

Primary porcine hepatocytes isolated and cultured according to the invention were found to metabolize ammonia and maintain both phase I and II detoxification functions for up to 10 days in vitro. In addition, the cultures showed proliferative activity both as an increase in total protein content and by $^3$H-thymidine incorporation. These porcine hepatocytes are suitable for use as the biological component of perfusion devices such as artificial LADs, e.g., those described by Jauregui, H. in U.S. Pat. No. 5,043,260, hereby incorporated by reference, because of their unique ability to proliferate and maintain a diversity of hepatic functions in short-term in vitro culture.

Structure of Perfusion Device

Figure 12:
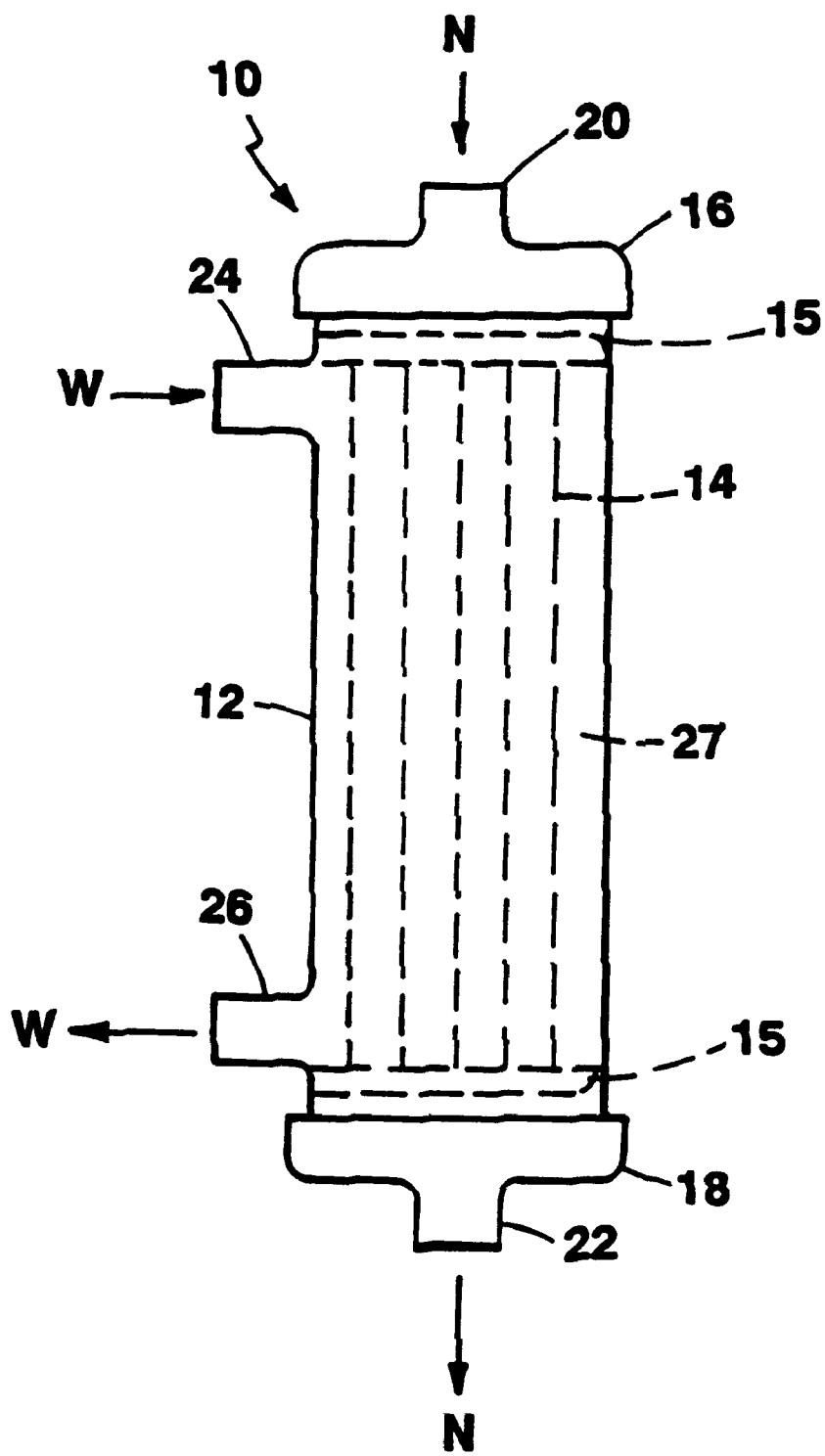
FIG. 12 is a diagram of a perfusion device.

FIG. 12 shows a perfusion device. The device includes a rigid, plastic outer shell 12, a plurality of hollow semipermeable membrane fibers 14 therein, and outer caps, 16 and 18. Fibers 14 are porous fibers. The upper and lower ends of hollow fibers 14 are potted in potting material 15 and thereby sealed to the inner surface of shell 12 near the upper and lower ends, employing techniques which are well known in the art. Cap 16 has perfusion inlet 20, and cap 18 has perfusion outlet 22, both of which communicate with the interiors of hollow fibers 14. Ports 24 and 26 are inward of potting 15 and provide access to the region within container 12 external of hollow fibers 14. Fibers 14 act as a barrier between perfusion compartment 25, inside of the fibers 14 and hepatocyte compartment 27, in the region between the exterior surfaces of fibers 14 and the inside of shell 12.

Artificial liver 10 is made from a standard shell provided with potted hollow fibers according to procedures well known in the art. Fibers 14 are made of membranes which include but are not limited to polyacrylic polyurethane, cellulose acetate or polysulfone polymer, have outer diameters between 150 $\mu$m and 400 $\mu$m, have inner diameters between 50 $\mu$m and 350 $\mu$m, and have pores of a size to have molecular weight cutoffs of 40,000 to 250,000 daltons. The outer surfaces of fibers 14 may be treated to facilitate attachment of cells, e.g., by treatment of the fibers with collagen, lectin, laminin, or fibronectin. The perfusion device may be regenerated by removing the hepatocytes from the hepatocyte compartment and replenishing the compartment with a fresh aliquot of porcine hepatocytes isolated and cultured as described above.

Reagents

The following reagents were used in isolation and culture of hepatocytes:

Chee's essential media (CEM), gentamicin, and FBS were purchased from GIBCO (Grand Island, N.Y.); insulin was purchased from Eli Lilly (Indianapolis, Ind.); and dexamethasone was purchased from Elkins-Sinn (Cherry Hill, N.J.). Vitrogen was obtained from the Collagen Corporation (Palo Alto, Calif.); collagenase from Worthington Biochemical Corporation (Freehold, N.J.); and HEPES from Research Organics, Inc. (Cleveland, Ohio). All other chemicals were obtained from Sigma Chemical Co. (St. Louis, Mo.), Aldrich Chemical (Milwaukee, Wis.) or J. T. Baker (Medford, Mass.) unless otherwise noted. Acetaminophen metabolites were obtained from McNeil Pharmaceuticals (Fort Worth, Pa.).

Hepatocyte Isolation

Female Yorkshire swine (approximately 12 kg body weight) were purchased from Earle Parsons (Hadley, Mass.). To induce diazepam and/or 7-EC metabolic enzymes in porcine hepatocytes prior to isolation, the swine may be fed inducers such as phenobarbitol or methylcholanthrene. Prior to the start of surgery, the swine were sedated with a combination of ketamine (25 mg/kg) and xylazine (2 mg/kg) followed by thiopental sodium. Heparin (3000 units) was administered intravenously. Pigs were intubated and maintained on a respirator supplemented with $O_2$ (1 L/min).

The digestion procedure was performed in situ. Retrograde perfusion (vena cava) of oxygen-saturated calcium-free buffer (see Table 1) at 37° C. was initiated at a rate of 200 ml/minute. After two minutes, the flow rate was reduced to 100 ml/minute and continued until the liver was blanched. The flow was temporarily stopped and perfusion with $O_2$-saturated buffered collagenase solution (see Table 1) was started. The perfusion was continued at 65 ml/minute for 20–30 minutes. After digestion, the liver was removed and transferred to a sterile beaker. The entire liver was quickly chilled with 4° C. washing buffer.

TABLE 1

Composition of Buffers Used For Hepatocyte Isolation*

|  | $Ca^{2+}$-free Perfusion Buffer | Buffered Collagenase Solution | Washing Buffer |
|---|---|---|---|
| NaCl | 8.3 | 3.9 | 8.3 |
| KCl | 0.5 | 0.5 | 0.5 |
| $CaCl_2 \cdot 2H_2O$ | — | 0.7 | 0.18 |
| HEPES | 2.4 | 24.0 | 2.4 |
| Collagenase | — | 0.5 | — |
| pH | 7.4 | 7.6 | 7.4 |

*Salt concentrations given in g/l of final solution.

To harvest the cells, the liver was cut into approximately one $cm^3$ pieces and suspended in washing buffer. The resulting suspension was filtered through a #10 wire screen (1.9 mm). The strained cell suspension was further filtered through a 253 $\mu$m nylon mesh. The final suspension was centrifuged at 7×g for 5 minutes at 4° C. to separate intact parenchymal cells from cell debris, damaged hepatocytes, and nonparenchymal cells (which are left in the supernatant). The supernatant was aspirated and the cell pellet was resuspended in 4° C. washing buffer. The washing procedure was repeated twice. The final cell pellet was resuspended in approximately 150 ml of tissue culture media. The final volume of cell suspension was approximately 400–500 ml at a density of 30–40×$10^6$ cells/ml. Aliquots of this suspension were used for viability assessment, e.g., trypan blue exclusion and LDH leakage as described by Jauregui et al., 1981, In Vitro 17:1100–1110, hereby incorporated by reference. Typical cell yields were 17×$10^9$±5×$10^9$ with a mean viability of 79±6%. The cell suspension was maintained at 4° C. until use.

Tissue Culture of Porcine Hepatocytes

Vitrogen (Collagen Corp., Palo Alto, Calif.) was diluted to 90–100 $\mu$g/ml in an aqueous solution containing 130 $\mu$g/ml of the coupling agent, carbodiimide [(1-cyclohexyl-3-2(2-morpholinoethyl carbodiimide-metho-p-toluene sulfonate)] using known methods, e.g., Naik et al., 1992, Cell Transplantation 1:61–69, hereby incorporated by reference. For monolayer culture, 2 mls of this solution were used to cover the surface of the tissue culture plasticware (Nunc Permanox, Baxter, Edison, N.J.) and incubated at 37° C. overnight. The dishes were rinsed with physiological saline and stored at 4° C. until use. Isolated hepatocytes were diluted to a concentration of 8×$10^5$ cells/ml in CEM media supplemented with: 10% FBS, 10 mU/ml insulin, 1 $\mu$M dexamethasone and 50 $\mu$g/ml of gentamicin. Five-ml aliquots (total seeding 4×$10^6$ cells per dish) were dispensed into 60-mm culture dishes (precoated with Vitrogen as described). The hepatocytes were allowed to attach for no more than 3 hours at 37° C. in a 5% $CO_2$-30% $O_2$ atmosphere at 90% relative humidity. The media was changed at 3 hours and at 2 day intervals thereafter. The cells were maintained at 37° C. in an atmosphere of 95% air, 5% $CO_2$ and 90% relative humidity after the initial 3 hour attachment.

Attachment of porcine hepatocytes to hollow fibers or other support compositions in a perfusion device may also be carried out by coating the fibers or other support with collagen, e.g., Vitrogen, and seeding the device with hepatocytes according to methods known in the art. The fibers may also be coated with lectins, as described in the art, e.g., Jauregui, H. in U.S. Pat. No. 5,043,260, hereby incorporated by reference.

For roller bottle hepatocyte culture, isolated hepatocytes were suspended at 8×$10^5$ cells/ml in CEM media supplemented with 10% FBS, 10 mU/ml insulin, 1 $\mu$M dexamethasone, and 50 $\mu$g/ml gentamicin. Aliquots of this cell suspension were placed in roller bottles containing microcarriers. The hepatocyte cultures were maintained at 37° C. in an atmosphere of 95% air, 5% $CO_2$+30% oxygen and a relative humidity of 90%. The medium was replaced at 48 hour intervals. Roller bottles from 490–750 $cm^3$ in volume were rotated at 1.5 rpm on a Tecnomara Cellspin roller system during which time hepatocyte-microcarrier aggregrates adhered to the walls of the roller bottle.

Various microcarriers were tested: Pharmacia Cytodex 3 (Pharmacia, Inc., Piscataway, N.J.), Nunc Biosilon (Nunc, Inc., Naperville, Ill.), Solohill Engineering Collagen Coated (Solohill Engineering, Inc., Ann Arbor, Mich.), Solohill Engineering Polyhipe Microporous (Solohill Engineering, Inc., Ann Arbor, Mich.), and Sigma gelatin microcarrier beads (Sigma Chemical Co., St. Louis, Mo.). Isolated hepatocytes were seeded in roller bottles on microcarriers at densities of $4\times10^6$ cells/ml of packed bead volume. Isolated hepatocytes attached to microcarriers may also be used as the biological component of perfusion devices such as LADs. Proliferation and metabolic function of hepatocytes cultured on microcarriers in roller bottles as well as in monolayer cultures were measured as described below.

Biochemical Assays

Hepatocyte cultures were evaluated for differentiated enzyme function on days 1, 2, 4, 6, 10 days (and following) in vitro. Unless otherwise noted, the following substrates were added to hepatocyte cultures and incubated for 3 hours prior to evaluating viability and/or metabolic activity: diazepam (50 $\mu$g/ml), 7-EC (50 $\mu$g/ml), acetaminophen (5 mM; 0.75 mg/ml), and ammonia (1.5 mM; 0.08 mg/ml $NH_4Cl$). A media control was incubated simultaneously under similar conditions but without cells. Thymidine incorporation by cultured hepatocytes was measured to assess cell proliferation in vitro. With the exception of ammonia media, media from cell cultures, i.e., culture supernatants, were collected and stored at –30° C. until assayed. After removal of the culture supernatants, the culture plates were rinsed 3 times with phosphate buffered saline (PBS) and reserved for protein determination by known methods, e.g., Hayner et al. 1982, Tissue Culture Methods 7:77–80.

Diazepam metabolic activity was measured as follows: $4\times10^6$ cells were cultured in a monolayer in 5 mls of medium containing 50 $\mu$g/ml diazepam, and the amount of diazepam metabolites present in the culture supernatant measured after 3 hours of culture. Diazepam metabolites were assayed by high performance liquid chromatography (HPLC) using a C18 $\mu$-Bondpack reverse phase column according to known methods, e.g., Jauregui et al., 1991, Xenobiotica 21:1091–1106, hereby incorporated by reference.

7-EC metabolism was measured as follows: $4\times10^6$ cells were cultured in a monolayer in 5 mls of medium containing 50 $\mu$g/ml 7-EC, and the amount of 7-hydroxycoumarin present in the culture supernatant measured after 3 hours of culture. 7-hydroxycoumarin levels were assayed using a C18 $\mu$-Bondpack reverse phase HPLC column according to known methods, e.g., Jauregui et al., 1991, Xenobiotica 21:1091–1106.

Acetaminophen and its metabolites were determined by ion-pairing HPLC using a C18 reverse phase column. Acetaminophen metabolism was measured as follows: $4\times10^6$ cells were cultured in a monolayer in 5 mls of medium containing 5 mM acetaminophen (0.756 mg/ml), and the amount of acetaminophen glucuronide present in the culture supernatant measured after 3 hours of culture. Acetaminophen and its metabolites, e.g., acetaminophen glucuronide, were determined by ion-pairing high performance liquid chromatography, e.g, using the method of Colin et al., 1986, J. Chromatogr. 377:243–251, hereby incorporated by reference. Acetaminophen may also be metabolized via a sulfonation pathway; metabolites may be assayed using methods known in the art.

Ammonia metabolism was measured as follows: $4\times10^6$ cells were cultured in a monolayer in 5 mls of medium containing 1.5 mM $NH_3$ (0.08 mg/ml $NH_4Cl$), and the amount of $NH_3$ present in the culture supernatant measured after 3 hours of culture. Ammonia media was processed immediately according to methods known in the art, e.g., using the commercial analyzer, Ektachem, manufactured by Kodak Corp. Rochester, N.Y. Ammonia metabolism is detected by measuring the amount of ammonia remaining in the culture supernatant after 3 hours of culture. If the hepatocytes are non-functional or losing viability, the initial level of ammonia typically increases over the culture period, reflecting the release of ammonia by dead cells. In contrast, viable, functional hepatocytes isolated and cultured as described above are typically capable of reducing the level of ammonia in the media at the beginning of the culture by at least 40% (up to about 70%) during a culture period of about 3 hours.

Detoxification of lidocaine may also be used to assess the functional capability of cultured hepatocytes in a perfusion device. Lidocaine metabolism was measured using known methods, e.g., Jauregui et al., 1995, Hepatology 21:460–469, hereby incorporated by reference. For example, $4\times10^6$ cells were cultured in a monolayer in 5 mls of medium containing 20 $\mu$g/ml lidocaine, and the amount of lidocaine metabolite, e.g., monoethylglycinexylidide (MEGX) present in the culture supernatant was measured after 3 hours of culture. Metabolism of lidocaine was tested using a TDX Analyzer manufactured by Abbott Diagnostics Laboratories, No. Chicago, Ill.

Acetaminophen, lidocaine, 7-EC, and ammonia metabolism may also be assessed in roller bottle cultures using methods described above for monolayer cultures. For example, the test compound, i.e. substrate, was added to roller bottle media at concentrations equivalent to that used for monolayers, e.g., acetaminophen, 0.75 mg/ml; lidocaine, 20 $\mu$g/ml; 7-EC, 50 $\mu$g/ml; and ammonia, 0.08 mg/ml. Presence of substrate metabolites or reduction in the level of ammonia in the culture media is then measured as described above.

Immunocytochemical Staining

Freshly isolated cells as well as cultured cells were fixed with absolute acetone and then stained to characterize cell type. The cells were then cytospun onto pretreated slides (Superfrost/plus, Fisher Scientific, Pittsburgh, Pa.) and stained with mouse anti-keratin-8 and mouse anti-keratin-18 (Amersham, Arlington Heights, Ill.), anti-vimentin (BioGenex Laboratories, San Ramon, Calif.), anti-actin (Sigma Chemical, St. Louis, Mo.), anti-keratin-19, and anti-desmin (BioGenex Laboratories), incubated for 30 min at 37° C. After rinsing with PBS, bound immunoglobulin was detected by further incubation for 30 min with FITC-conjugated goat globulins directed against mouse IgG (Sigma). The slides were stained with propidium iodide (Sigma) to show nuclei. These procedures were used to investigate the percentage of hepatocytes (anti-keratin-$8^+$ and anti-keratin-$18^+$), fibroblasts, and endothelial cells (anti-vimentin$^+$). In addition, smooth muscle cells (anti-actin$^+$), bile duct cells (anti-keratin-$19^+$), and Ito cells (anti-desmin$^+$) were also identified.

Percentage of pericentral cells in hepatocyte cultures was determined by staining the cells for the marker enzyme, glutamine synthetase.

EXAMPLE 1
Proliferation of isolated primary porcine hepatocytes in vitro

Figure 1:
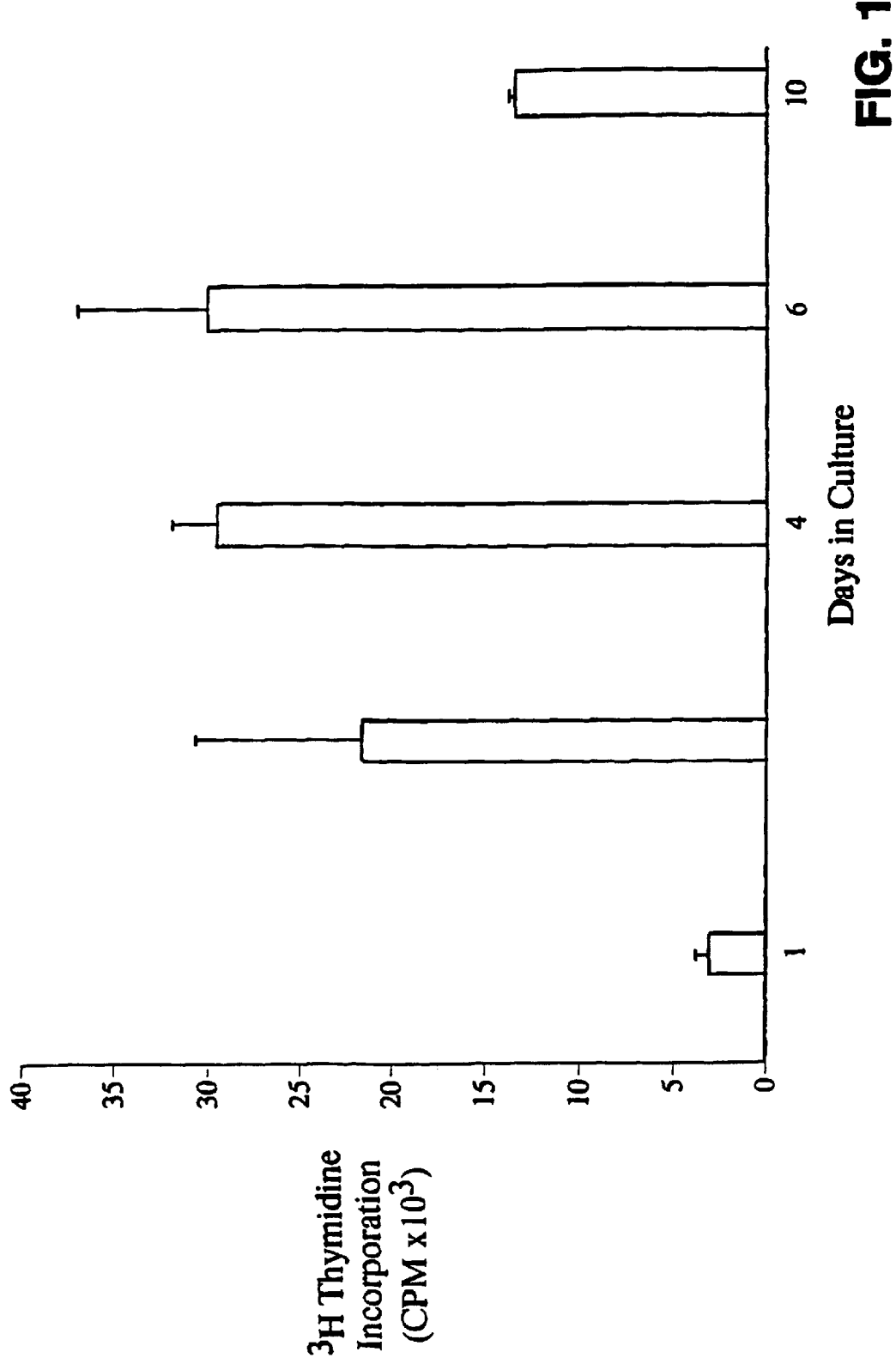
FIG. 1 is a bar graph showing incorporation of $^3$H-thymidine vs. days in culture (n=3).

Tritiated thymidine incorporation by porcine liver cells in culture was measured over 24 hour intervals on days 1, 2, 4, 6, 10 (and following). Although proliferative activity was minimal on day 1, $^3$H-thymidine uptake increased 6-fold by day 2 and continued to increase through day 6 (FIG. 1). Thymidine incorporation on day 6 was nearly 10 times that of the first 24 hours, and proliferative activity in cultured cells was still detectable through culture day 10.

Figure 3B:
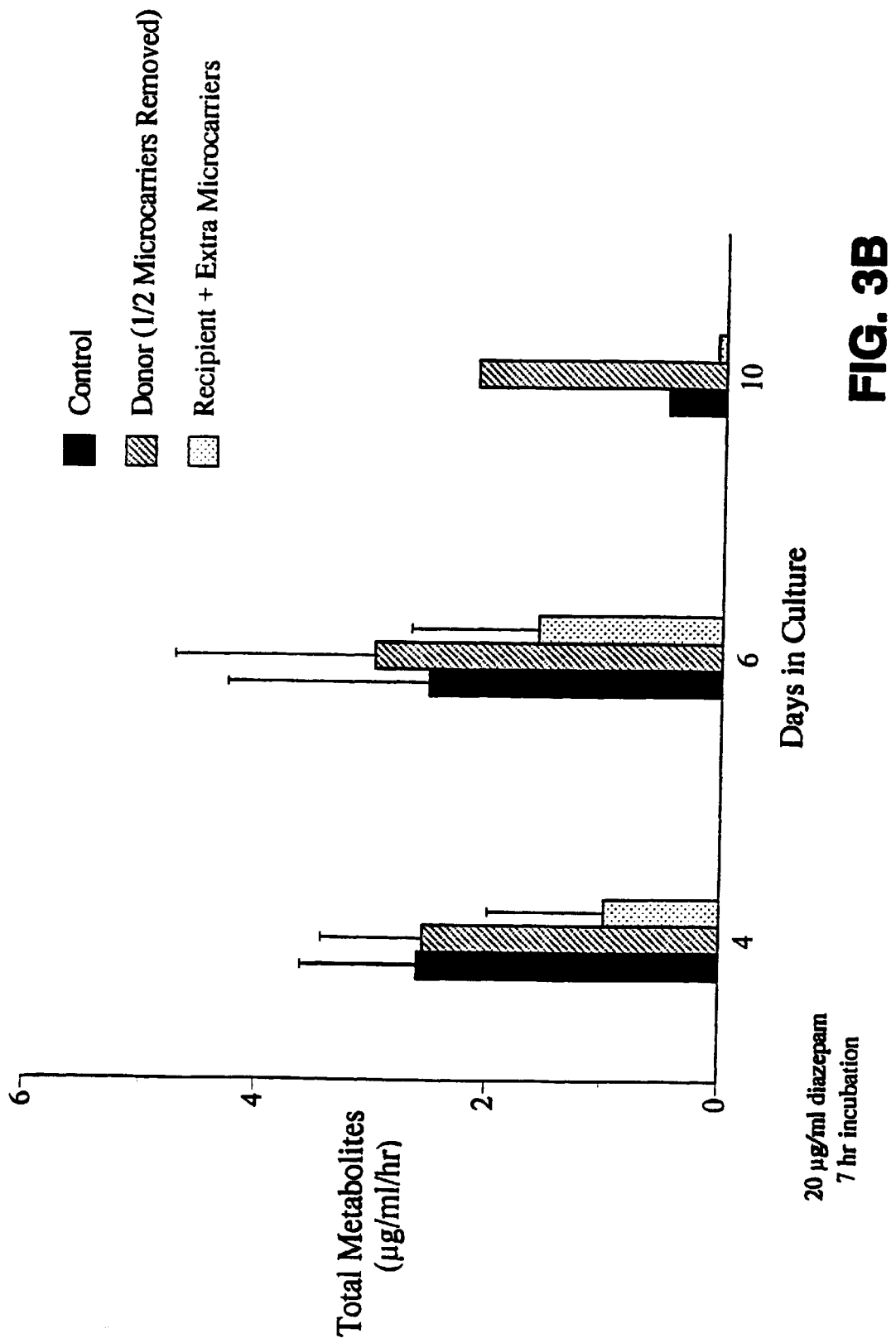
FIG. 3B is a bar graph showing diazepam metabolic activity of porcine hepatocytes seeded in roller bottles.

$^3$H-thymidine incorporation by hepatocytes in roller bottle culture was measured to show hepatocyte proliferation throughout the days in culture (FIG. 3A). Proliferation was detected for up to 20 days in culture, peaking at 4–6 days and gradually declining by 10–15 days.

Figure 2:
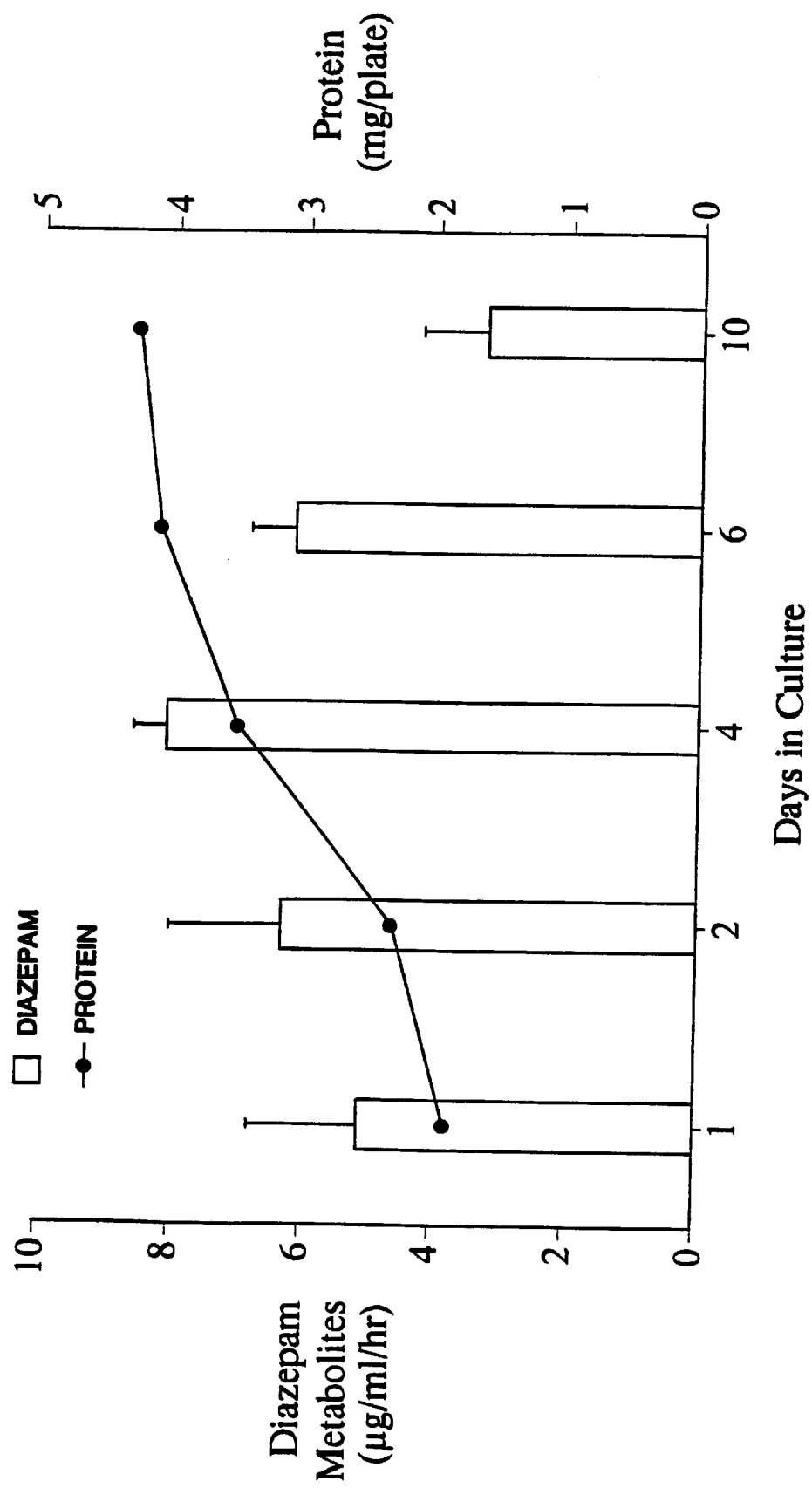
FIG. 2 is a bar graph showing total diazepam metabolites (oxazepam, nordiazepam and temazepam) vs. days in culture. Open bars represent mean±SD of 3 experiments. The line represents the mean protein content of all cultures used in diazepam, 7-EC, acetaminophen, and ammonia metabolism studies (n=12).

EXAMPLE 2
Metabolic activity of isolated primary porcine hepatocytes in vitro Peak diazepam metabolism (expressed as the total of metabolites temazepam, nordiazepam, and oxazepam) was highest on culture day 4 (FIG. 2). After day 6, diazepam metabolism gradually decreased but was still detectable at day 10. Although a pattern of cell proliferation was seen by $^3$H thymidine uptake (FIG. 1) and total protein content of the hepatocyte monolayer cultures (FIG. 2), diazepam metabolism did not follow the observed trend. These findings suggest that (a) cells other than hepatocytes were growing in these cultures and/or (b) the porcine hepatocytes are lacking substrates or other tissue culture conditions necessary to maintain P450 detoxification functions.

Figure 3C:
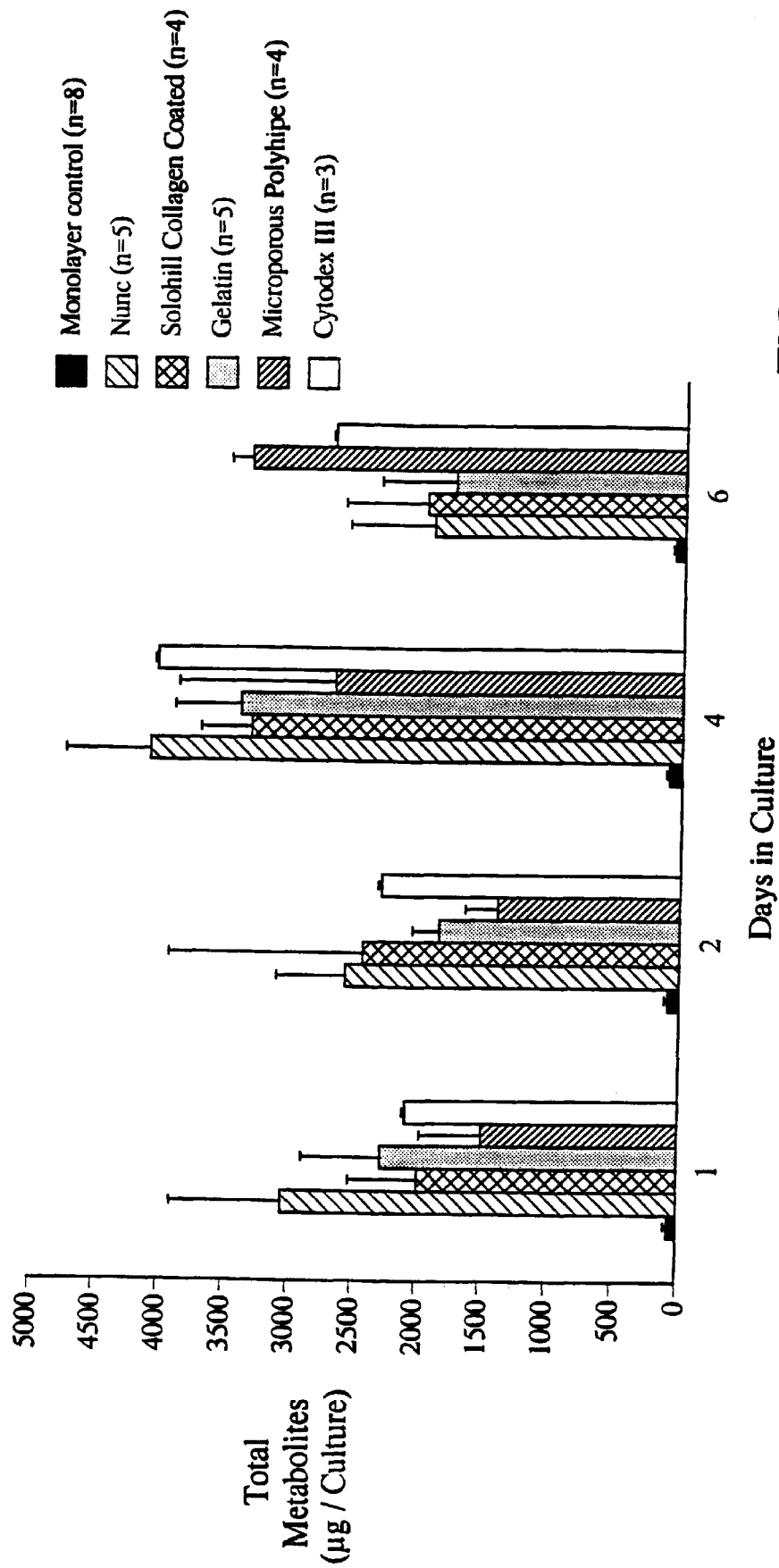
FIG. 3C is a bar graph showing diazepam metabolic activity of porcine hepatocytes seeded on various types of microcarriers and cultured in roller bottles.

To measure metabolic activity of hepatocytes cultured on microcarriers in roller bottles, the media to hepatocyte ratio was increased 50% (compared to cultures used for proliferation assays described above) by the removal of half of the seeded microcarriers after 24 hr in culture while maintaining the same media volume. Upon removal, the seeded microcarriers were transferred to a roller bottle containing additional unseeded microcarriers thereby halving the cell to microcarrier ratio. The control roller bottle cultures were maintained at constant cell-media-microcarrier ratio. Hepatocyte function in roller bottle cultures was assessed by measuring diazepam metabolism (FIG. 3B), and the metabolic activity of roller bottle cultures was compared to that of monolayer cultures (FIG. 3C).

These data indicate that culturing isolated porcine hepatocytes on microcarriers in roller bottles allows the replication of hepatocytes without loss of their detoxification activity. The data also indicate that porcine hepatocytes cultured using the microcarrier-roller bottle system have a more efficient detoxification capacity than either freshly isolated cells or cells cultured by other conventional methods. Porcine hepatocytes grown under these conditions in sufficient numbers are suitable for use in perfusion devices such as LADs and eventual seeding at patient treatment centers. This culture technique also facilitates the production of hepatocyte populations that can be further expanded by culturing the microcarrier-seeded hepatocytes within the perfusion device, e.g., a collagen-treated LAD, so that the devices may be shipped to medical centers completely assembled with hepatocytes growing in the devices themselves.

As a result of the increased metabolic efficiency of these cells, fewer microcarrier-cultured hepatocytes are needed per perfusion device to perform the same function compared to conventionally cultured cells. The increased capacity of hepatocytes to proliferate in roller bottles would reduce the overall cost of perfusion devices and the extended culture period (up to 15 days) would allow for quality control testing to be performed prior to distribution to treatment centers without compromising the therapeutic function of the device.

EXAMPLE 3
Prolonged viability and function of hepatocytes cultured in supplemented media Porcine hepatocytes were cultured with the following media formulations to evaluate the effect of FBS and DMSO on cell viability and diazepam metabolism: (1) CEM supplemented with 10% FBS, 10 mU/ml insulin, 1 µM dexamethasone and 50 µg/ml of gentamicin; (2) CEM supplemented with 5% FBS, 2% DMSO, 10 mU/ml insulin, 1 µM dexamethasone and 50 µg/ml of gentamicin; (3) CEM supplemented with 2% FBS, 2% DMSO, 10 mU/ml insulin, 1 µM dexamethasone and 50 µg/ml of gentamicin; (4) CEM supplemented with 2% DMSO, 10 mU/ml insulin, 1 µM dexamethasone and 50 µg/ml of gentamicin (0% FBS); and (5) CEM supplemented with 10 mU/ml insulin, 6.25 µg/ml transferrin, 6.25 µg/ml selenium (ITS), 50 µg/ml gentamicin, 1 µM dexamethasone, 2% DMSO (0% FBS).

Figure 11A:
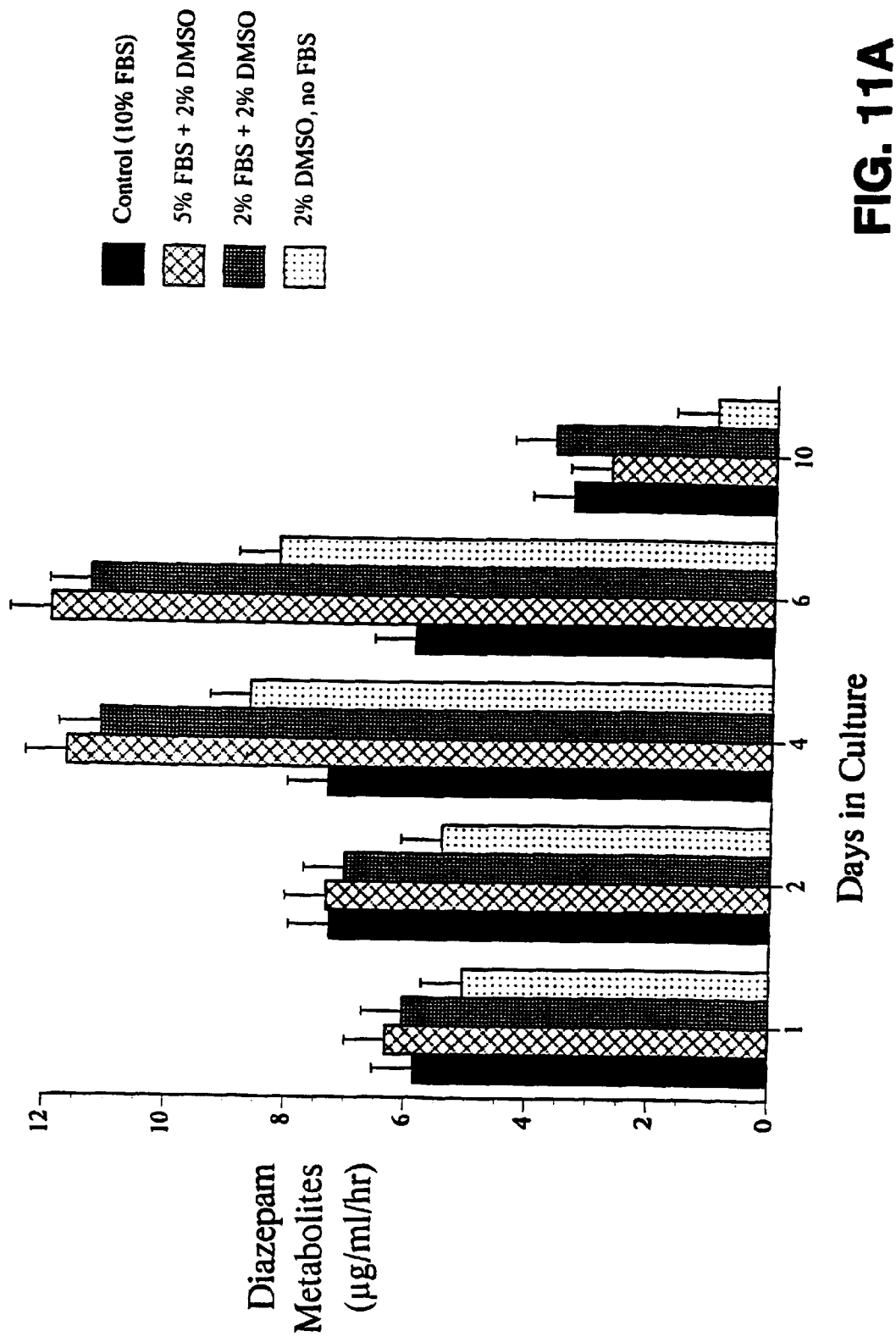
FIG. 11A is a bar graph showing diazepam metabolic activity in standard culture media containing 10% FBS, standard culture media containing 5% FBS+2% DMSO, and standard culture media containing insulin, transferrin, selenium and 2% DMSO (in the absence of FBS).
Figure 11B:
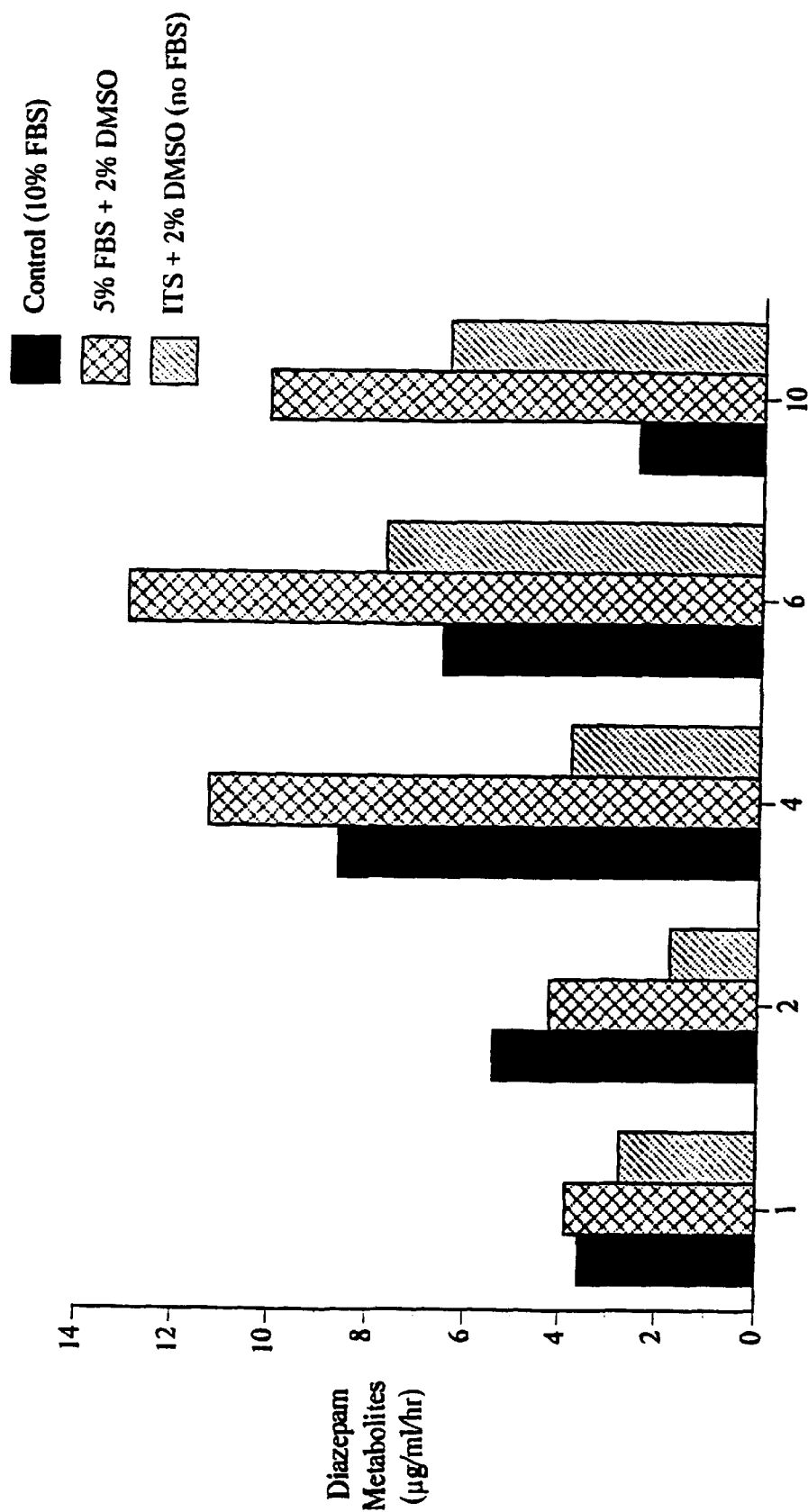
FIG. 11B is a bar graph showing diazepam metabolic activity in standard culture media containing 10% FBS, standard culture media containing 5% FBS+2% DMSO, standard culture medium containing 2% FBS+2% DMSO, and standard culture medium containing 2% DMSO (in the absence of FBS).

As shown in FIGS. 11A and 11B, the requirement for FBS in the culture media of porcine hepatocytes is reduced by the addition of DMSO. Diazepam metabolic activity by porcine hepatocytes cultured in the presence of DMSO was found to be greater than that by porcine hepatocytes cultured in 10% FBS-supplemented media (FIG. 11A). Diazepam metabolic activity was detected for up to 10 days of culture and peaked at 4–6 days of culture. Hepatocytes cultured in ITS medium supplemented with 2% DMSO (in the absence of FBS) were found to proliferate for up to 10 days; diazepam metabolism was detected through 10 days, peaking at 6 days. At 6–10 days, diazepam metabolism was at least 2 times the level seen in control cultures (FIG. 11B). These data indicate that metabolic activity of isolated porcine hepatocytes can be optimized for use in perfusion devices such as LADs by culturing the hepatocytes in DMSO-supplemented media (in the presence or absence of FBS).

Absence of FBS in the culture media of porcine hepatocytes represents an additional advantage of the invention by reducing the cost of culture and eliminating the variability of culture, e.g., variations in growth-promoting activity between lots of FBS, often associated with organic culture media supplements such as animal sera.

Figure 6A:
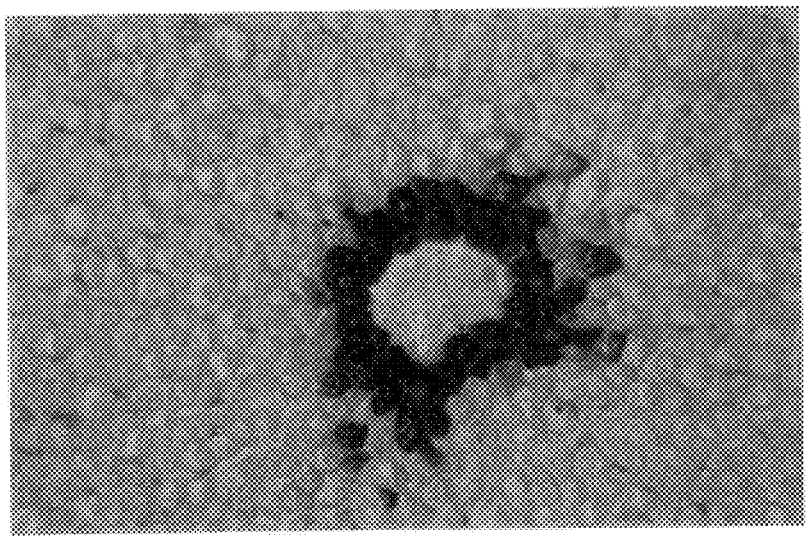
FIG. 6A is a photomicrograph of a liver tissue section showing pericentral cells (cells which stain positively for the marker enzyme, glutamine synthetase).
Figure 6B:
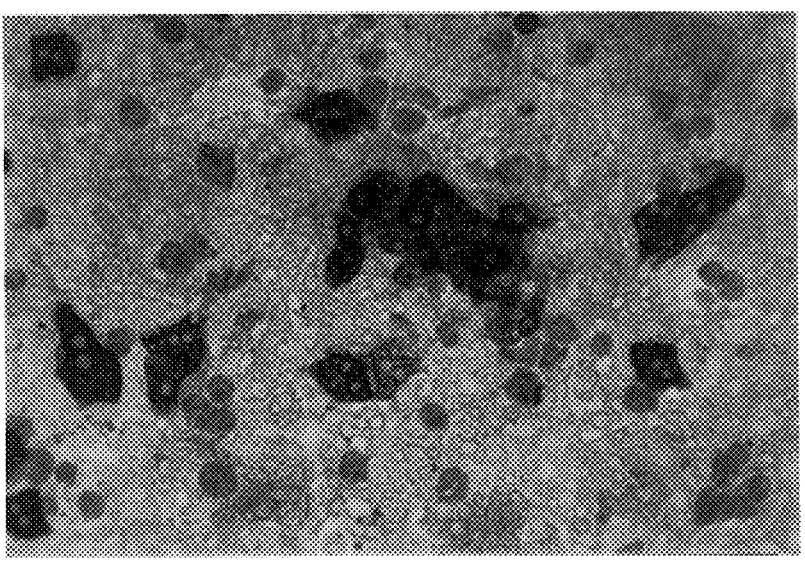
FIG. 6B is a photomicrograph of cells prepared by isolating porcine hepatocytes from livers using retrograde perfusion. Pericentral cells are shown as positively stained for glutamine synthetase.
Figure 6C:
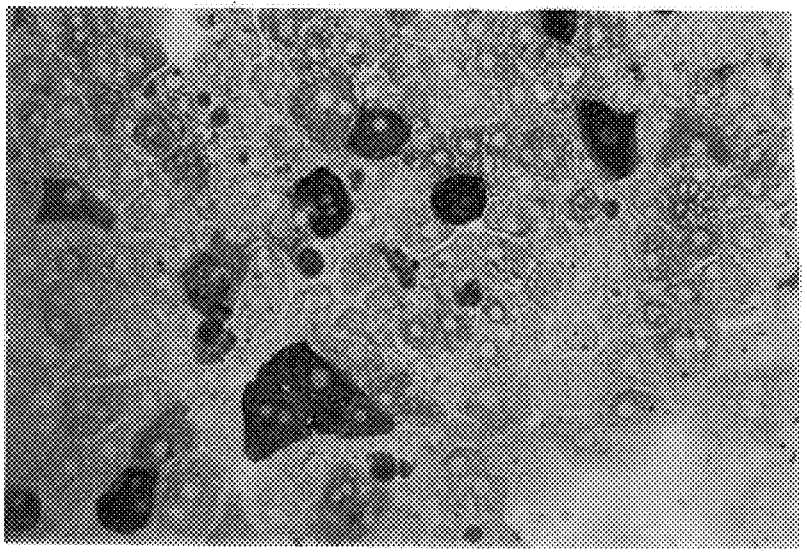
FIG. 6C is a photomicrograph of cells prepared by isolating porcine hepatocytes from livers using anterograde perfusion. Pericentral cells are shown as positively stained for glutamine synthetase.

EXAMPLE 4
Identification of cell types in a sample of isolated primary porcine hepatocytes Hepatocytes were stained for glutamine synthetase to identify pericentral cells in tissue sections and in samples of isolated and cultured porcine hepatocytes. The percentage of glutamine synthetase positive cells in whole tissue is typically 7–8% (FIG. 6A). Isolation of porcine hepatocytes by retrograde perfusion produces a population of hepatocytes containing 9–10% pericentral cells (FIG. 6B), whereas conventional anterograde perfusion routinely produces populations containing 7.5% pericentral cells (FIG. 6C). These data indicate that isolation of porcine hepatocytes using retrograde liver perfusion consistently yields a higher percentage of highly metabolically-active pericentral cells suitable for use as the biological component in perfusion devices.

Figure 4:
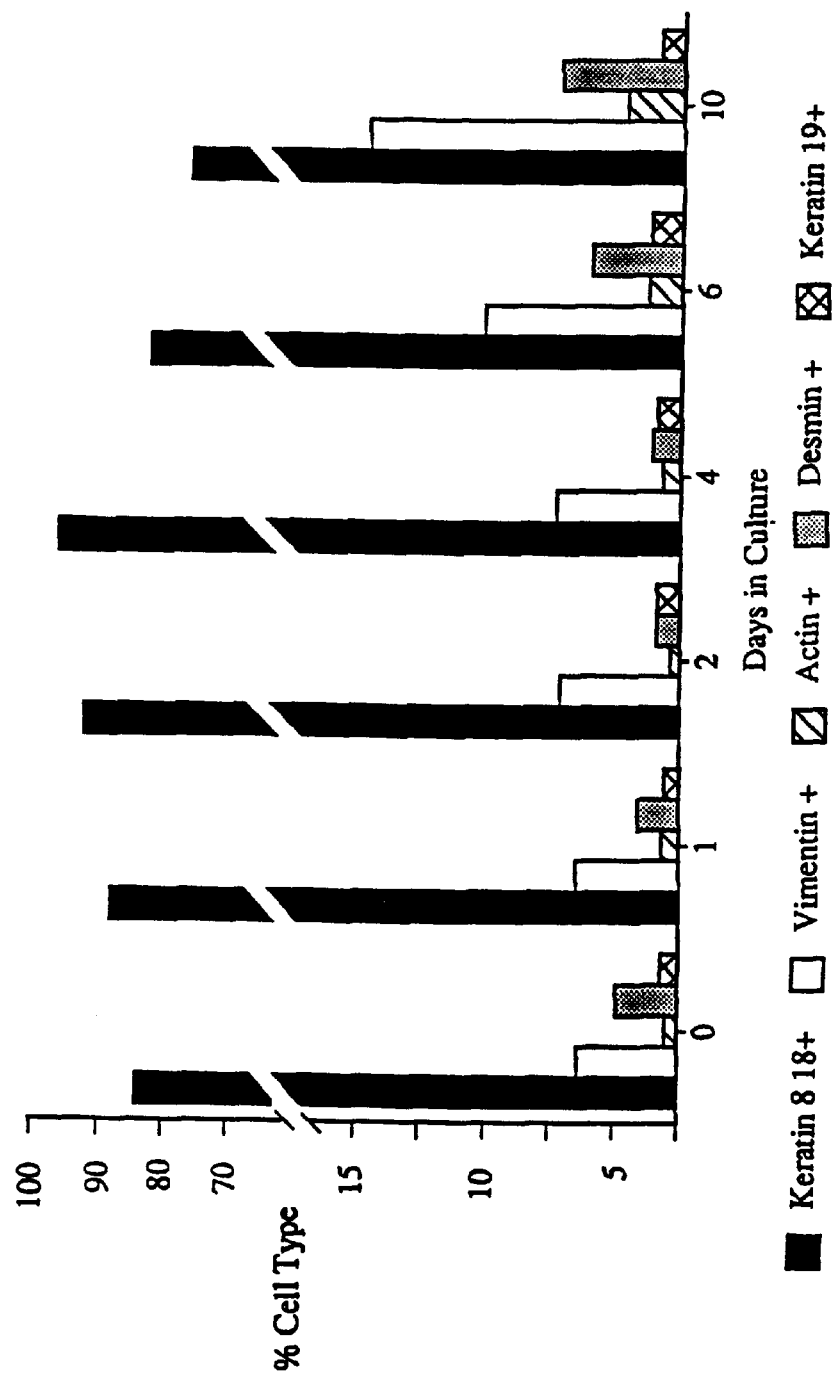
FIG. 4 is a bar graph showing percentages of various cell types at the time of isolation and through 10 days of culture. Immunofluorescent staining was carried out using the following antibodies: anti-keratin-8 and anti-keratin-18; anti-vimentin; anti-actin; anti-desmin; and anti-keratin-19. These antibodies detect hepatocytes, fibroblasts, Ito cells, smooth muscle cells and bile duct cells, respectively.
Figure 5A:
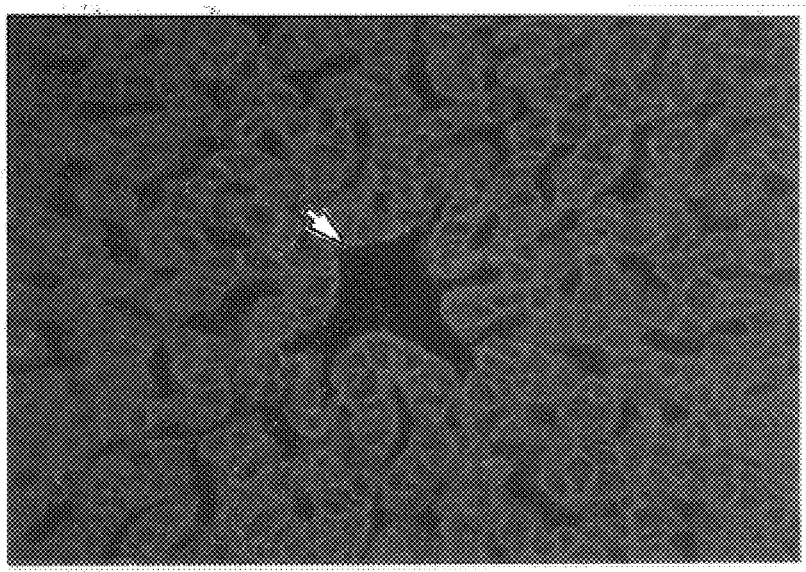
FIG. 5A is photomicrograph of a frozen section of porcine liver stained with mouse anti-keratin-8 IgG and mouse anti-keratin-18 IgG followed by fluoroscein isothiocyanate (FITC)-conjugated goat anti-mouse IgG. Arrowhead points to the central vein (×200).
Figure 5B:
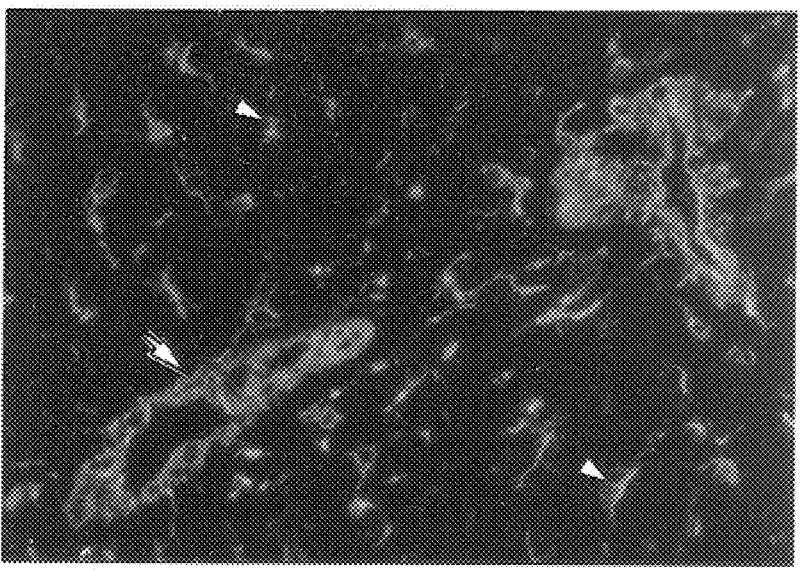
FIG. 5B is a photomicrograph of a frozen tissue section of porcine liver stained with mouse anti-vimentin IgG and FITC-conjugated goat anti-mouse IgG. Portal tract (large arrowhead) shows strong positive staining of fibroblasts. Small arrowheads show stained endothelial cells in sinusoidal areas (×200).
Figure 5C:
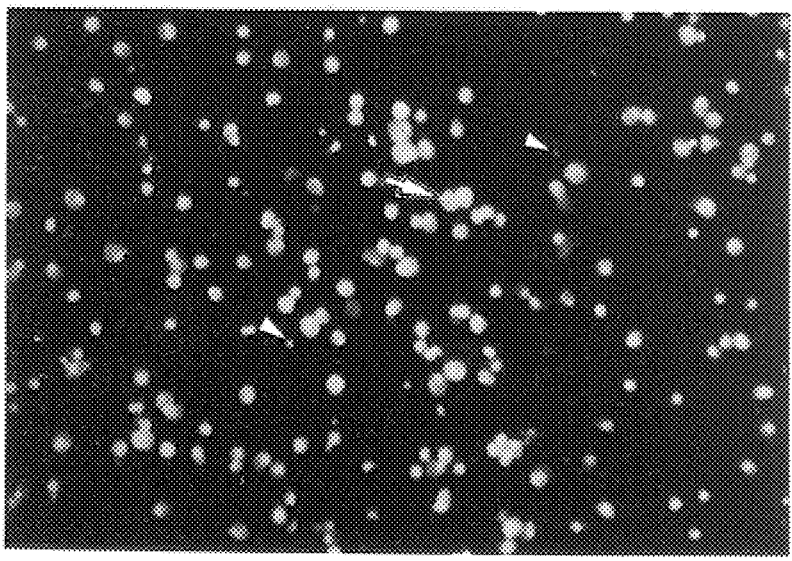
FIG. 5C is a photomicrograph of cells prepared from a 4-day porcine cell culture showing the nuclei of all cells stained with propidium iodide (small arrowheads) and the nuclei of hepatocytes stained with mouse anti-keratin-8 IgG and mouse anti-keratin-18 IgG followed by FITC-conjugated goat anti-mouse IgG (×100) as being surrounded by cytoplasmic keratin (large arrowhead).
Figure 5D:
FIG. 5D is a photomicrograph of cells prepared from 4-day porcine cell cultures (×100) and stained with mouse anti-vimentin IgG and FITC conjugated goat anti-mouse IgG (large arrowhead).
Figure 5E:
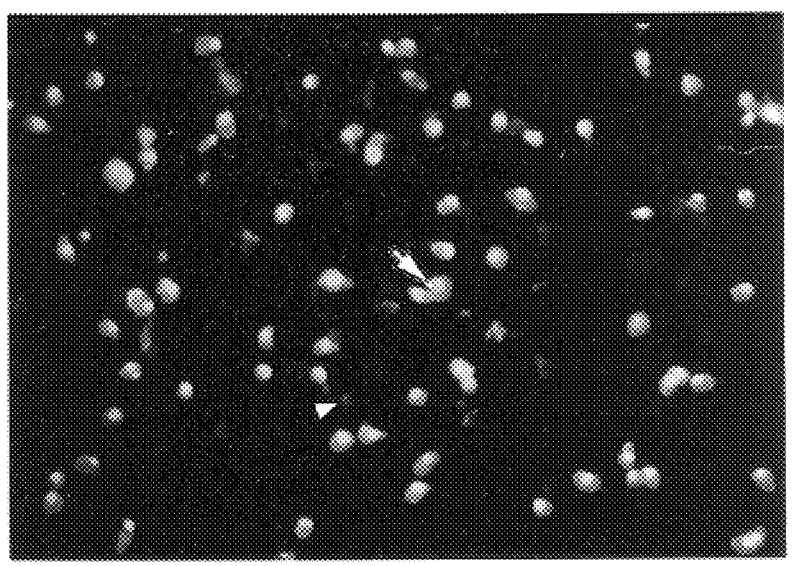
FIG. 5E is a photomicrograph of cells prepared from 10-day porcine cell cultures and stained as described for FIG. 5C (×120).
Figure 5F:
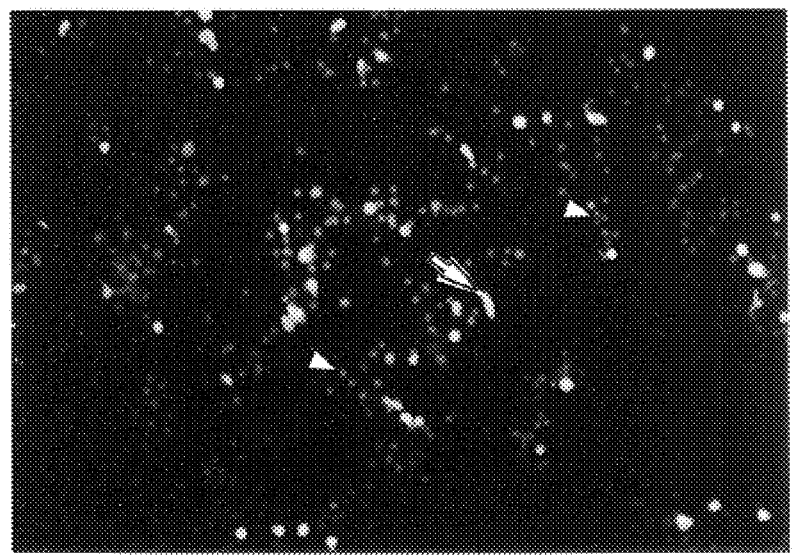
FIG. 5F is a photomicrograph of cells prepared from 10-day porcine cell cultures and stained as described for FIG. 5D (×100).

Immunocytochemical staining of the antigens, keratin-8, keratin-18, vimentin, desmin, actin and keratin-19, indicated the following distribution of cell types in the isolated sample of primary porcine hepatocytes: 85% hepatocytes, 4% fibroblasts/endothelial cells, 2% Ito cells, 0.5% smooth muscle cells, and 0.7% bile duct cells, respectively (FIG. 4). FIGS. 5A–5F shows representative fields of slides prepared from monolayer cultures on day 4 of in vitro culture.

By day 4, the percentage of hepatocytes was found to be 93%. The proliferation of nonparenchymal cells was found to contribute to the increase of the protein content of the monolayer cultures. Immunocytochemical staining identified cell proliferation through day 4 to be primarily hepatocytes, while days 6 and 10 showed nonparenchymal cells to be increasing. These data suggest that the increase of the total number of cells as measured by the protein assay was largely due to an increase in hepatocyte numbers. These results also indicate that the steep decline in diazepam metabolism reflects in part a loss of hepatocyte function by day 6.

EXAMPLE 5

Detoxification of drugs and endogenous metabolites by isolated primary porcine hepatocytes Currently, the most successful treatment for hepatic failure, orthotopic liver transplantation, is limited by the immediate availability of donor organs. In addition, transplantation may be unnecessary in some patients with acute liver failure in whom an actively regenerating liver requires only temporary support to avoid the development of HE. Methods to provide hepatic support have been attempted for many years, but none of the available therapies (e.g., hemoperfusion, hemodialysis, plasmapheresis, etc.) have improved patient survival. Porcine hepatocytes isolated and cultured as described above maintain a wide range of in vivo metabolic functions. Therefore, a perfusion device containing such hepatocytes can be used to support an acute liver failure patient either during hepatic regeneration or while awaiting transplantation.

The cause of HE, an often fatal outcome of fulminant liver failure, is undetermined, but it is likely that detoxification functions of the liver play an important role. Increases in endogenous benzodiazepine (bz) ligands may induce neural inhibition at the bz receptor thereby mediating HE. Neuroinhibitory substances induced in this manner have been identified in body fluids of HE patients. Alternatively, elevations in cerebral-spinal fluid and blood ammonia levels (seen in patients with acute liver failure) may result in the neuropathological changes of HE. Ammonia toxicity is widely accepted as the major factor precipitative to hepatic coma in patients with chronic liver failure.

Figure 7:
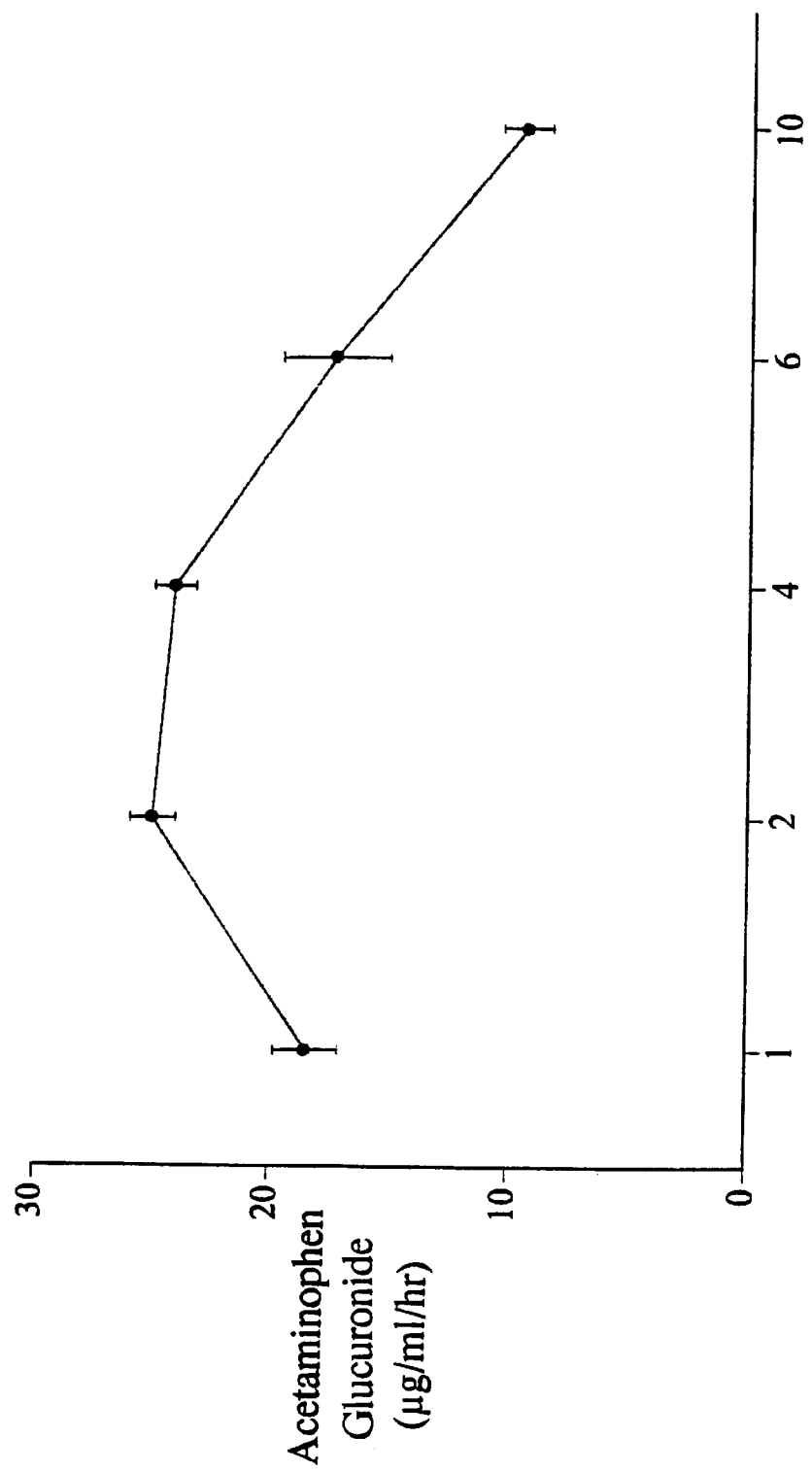
FIG. 7 is a line graph showing glucuronidation of acetaminophen by porcine hepatocytes vs. days in culture (n=3). Values represent mean±SD.
Figure 8:
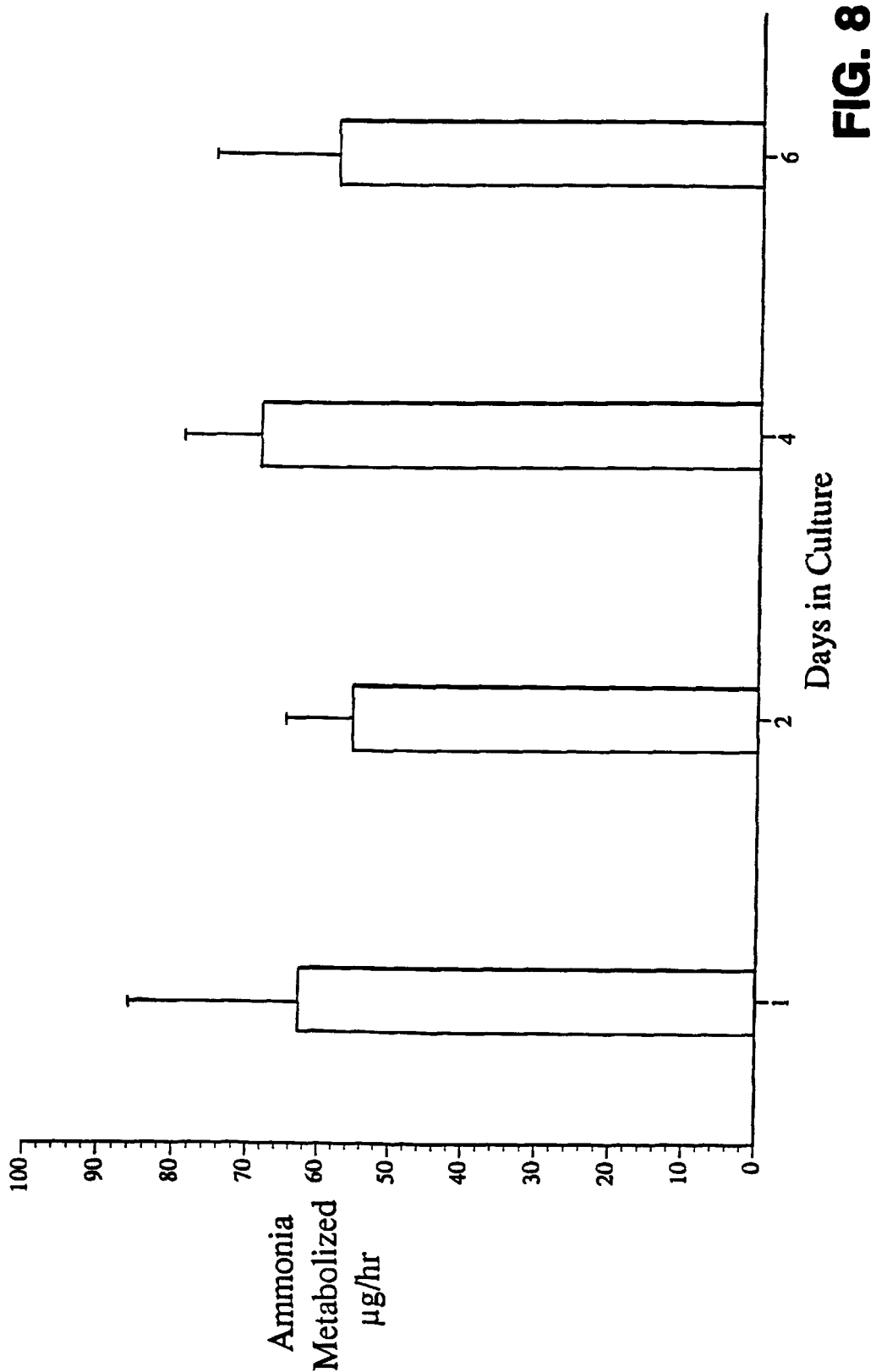
FIG. 8 is a bar graph showing ammonia metabolism by porcine hepatocytes vs. days in culture (n=3). Values represent mean±SD.
Figure 9:
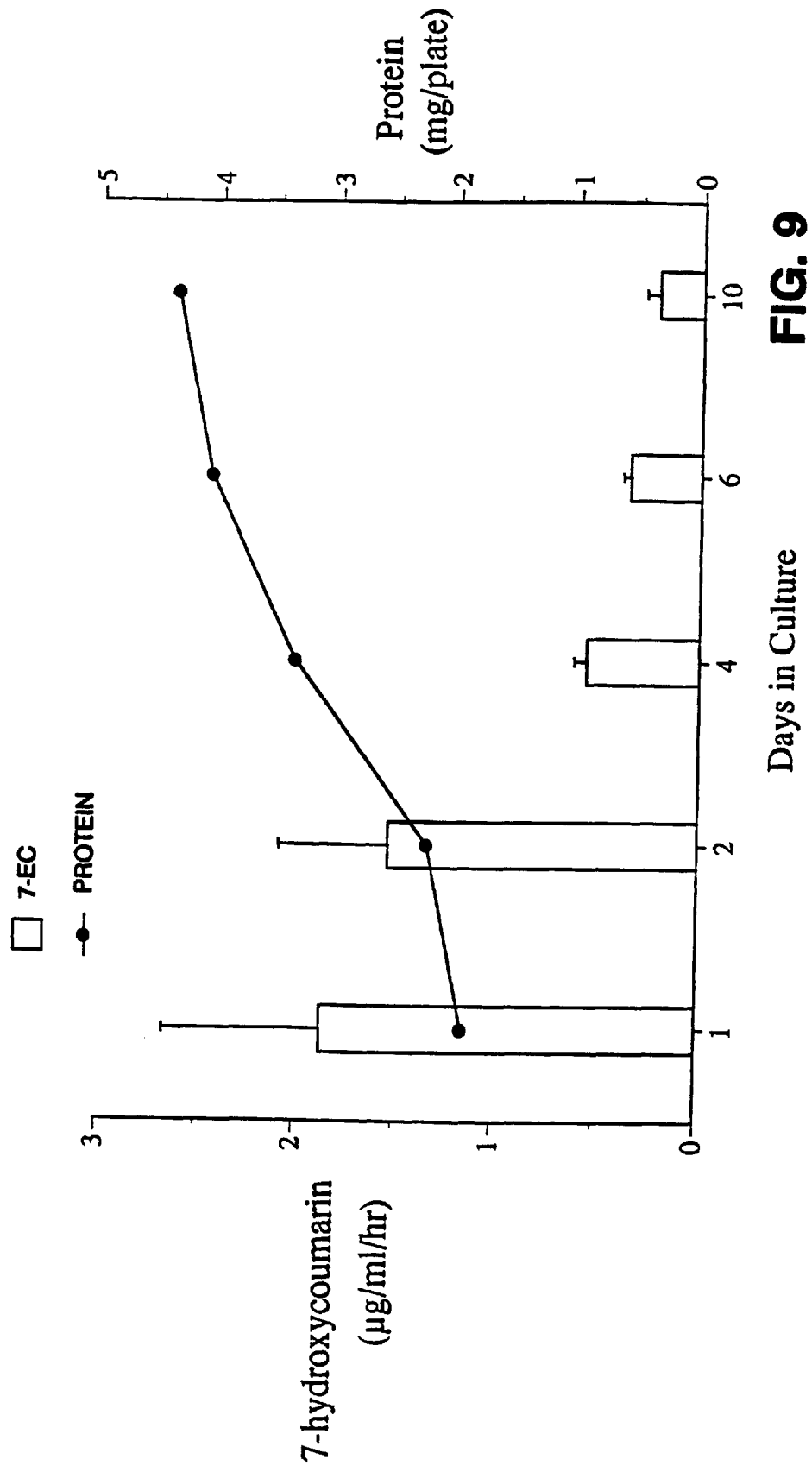
FIG. 9 is a bar graph showing the conversion of 7-EC to 7-hydroxycoumarin by porcine hepatocytes vs. days in culture (n=3). Values represent mean±SD.
Figure 10:
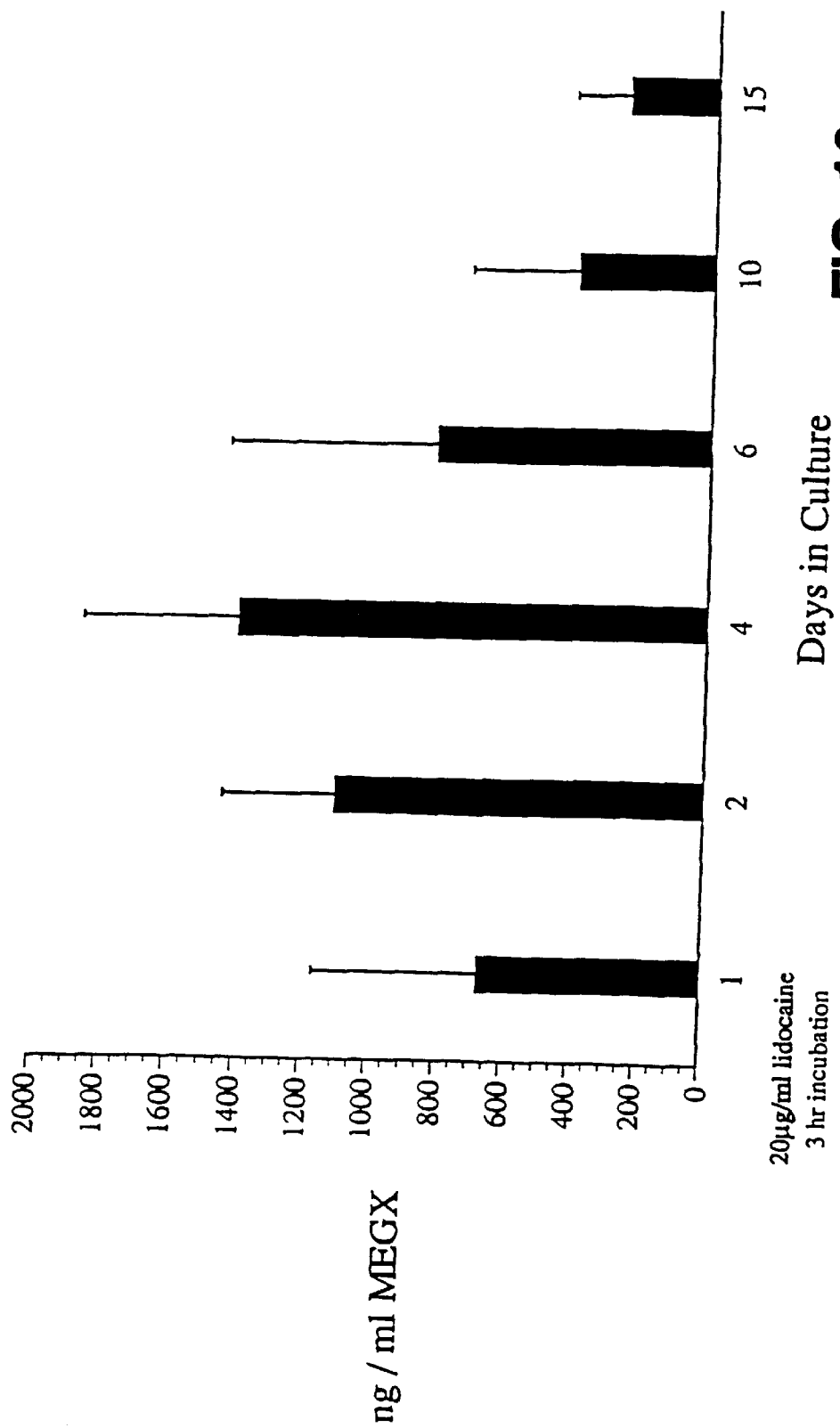
FIG. 10 is a bar graph showing lidocaine metabolism in porcine hepatocyte cultures.

Metabolism of benzodiazepines and ammonia as well as acetaminophen, 7-EC, and lidocaine by porcine hepatocytes isolated and cultured according to the invention was tested. Acetaminophen glucuronide production, a measure of active conjugative metabolism, was found to be highest on culture days 2 & 4 (FIG. 7). Although the assay was also capable of detecting the sulphate and mercapturate metabolites of acetaminophen, these metabolites were not detected. Ammonia metabolism was measurable through 10 days and peaked on day 4 (FIG. 8). Unlike the other detoxification functions evaluated, the conversion of 7-EC to 7-hydroxycoumarin was highest during the first 2 days and progressively decreased over the remaining culture period (FIG. 9). Lidocaine metabolism was detected for up to 15 days in culture and was highest on day 4 (FIG. 10). In summary, the metabolism of ammonia, diazepam and acetaminophen showed a similar trend, increasing through day 4 and gradually decreasing to day 10, while 7-EC metabolism decreased steadily beyond culture day 2.

The active metabolism of diazepam by porcine hepatocytes through 10 days in culture provides evidence of intact phase I and II metabolism in porcine hepatocytes isolated and cultured according to the invention. These data indicate that detoxification of diazepam and other compounds by cultured porcine hepatocytes is predictive of the therapeutic utility and efficacy of perfusion devices containing these cells to treat and prevent HE.

Acetaminophen metabolism by cultured hepatocytes provides evidence of intact conjugative function (phase II metabolism). As an important detoxification mechanism, conjugation of acetaminophen with sulfate or glucuronic acid accounts for 80–90% of the metabolic byproducts, the remainder being metabolized through the cytochrome P450 enzyme system. These data indicate that porcine hepatocytes, isolated and cultured as described above, metabolize acetaminophen, specifically by the glucuronidation metabolic pathway, through 10 days in culture.

Conversion of 7-EC to 7-hydroxycoumarin requires both phase I and phase II reactions. Failure of either pathway may account for 7-hydroxycoumarin production decrease over the culture period. Since glucuronidation activity remained intact through 10 days based on the production of acetaminophen glucuronide, the difference between 7-EC and diazepam metabolism (both metabolized by phase I & II) in vitro may be due to variance in the regulation of each P450 species, e.g., two different isoenzymes responsible for diazepam and 7-EC metabolism, (CYP2C18 and CYP2A6) respectively.

Additional detoxification function was demonstrated by ammonia metabolism measurable through day 10 in culture and lidocaine metabolism through day 15 in culture.

Other embodiments are within the following claims.

What is claimed is:

1. An isolated sample of primary porcine hepatocytes, comprising at least 9% pericentral cells, wherein said cells retain metabolic activity for at least 24 hours in vitro.

2. The sample of claim 1, wherein said sample comprises at least 10% pericentral cells.

3. The sample of claim 1, wherein said sample is characterized by:
    (a) diazepam metabolic activity of at least 3 $\mu$g/ml total diazempam metabolites per hour;
    (b) 7-ethoxycoumarin metabolic activity of at least 0.25 $\mu$g/ml 7-hydroxycoumarin per hour;
    (c) acetaminophen metabolic activity of at least 10 $\mu$g/ml acetaminophen glucuronide per hour;
    (d) $NH_3$ metabolism of at least 45 $\mu$g/ml $NH_3$ per hour; or
    (e) proliferative activity for at least 24 hours of in vitro culture.

4. The sample of claim 3, wherein said sample is characterized by:
    (a) diazepam metabolic activity of at least 8 $\mu$g/ml total diazempam metabolites per hour;
    (b) 7-ethoxycoumarin metabolic activity of at least 1.5 $\mu$g/ml 7-hydroxycoumarin per hour;
    (c) acetaminophen metabolic activity of at least 25 $\mu$g/ml acetaminophen glucuronide per hour;
    (d) $NH_3$ metabolism of at 60 $\mu$g/ml of $NH_3$ per hour; or
    (e) proliferative activity for at least 10 days of in vitro culture.

5. A method of isolating a sample of primary porcine hepatocytes enriched for pericentral cells, comprising
    (a) providing a pig;
    (b) perfusing a liver from said pig in a retrograde manner with a solution that is free of digitonin;

(c) removing said liver from said pig;

(d) retrieving said hepatocytes from said liver; and (e) separating said hepatocytes from cellular debris and non-parenchymal cells to yield said sample of hepatocytes, said sample comprising at least 9% pericentral cells, wherein said hepatocytes retain metabolic activity for at least 24 hours in vitro.

6. The method of claim 5, wherein said porcine liver is perfused with a buffered collagenase solution.

7. The method of claim 5, wherein step (b) is carried out in situ.

8. The method of claim 5, wherein said pig weighs at least 15 pounds.

9. The method of claim 8, wherein said pig weighs between 20–35 pounds.

10. The method of claim 5, wherein said pig is at least 6 weeks of age.

11. The method of claim 10, wherein said pig is between 6–8 weeks of age.

12. A method of enhancing viability and metabolic activity of porcine hepatocytes in vitro comprising:

(a) providing a sample of porcine hepatocytes in a suspension of particles; and (b) culturing said suspension in a roller bottle, wherein said hepatocytes and said particles form aggregates which adhere to the wall of said roller bottle and wherein said hepatocytes proliferate for at least 24 hours of in vitro culture and are at least 2 times more metabolically active than a second sample of porcine hepatocytes cultured in a monolayer.

13. The method of claim 12, wherein said particles are microcarrier beads.

14. The method of claim 12, wherein said hepatocytes proliferate for at least 10 days of in vitro culture and metabolize at least 20 times more of a toxic compound than a second sample of porcine hepatocytes cultured in a monolayer.

15. The method of claim 14, wherein said compound is diazepam.

16. The method of claim 12, wherein said suspension comprises a medium comprising at least 5% fetal bovine serum.

17. The method of claim 12, wherein said suspension comprises a serum-free medium.

18. The method of claim 12, wherein said suspension comprises a medium comprising at least 1% dimethyl sulfoxide.

19. The method of claim 18, wherein said medium comprises insulin.

20. The method of claim 18, wherein said medium comprises transferrin.

21. The method of claim 18, wherein said medium comprises selenium.

22. The method of claim 18, wherein said medium comprises insulin, transferrin, selenium, and at least 2% DMSO.

23. The sample of claim 1, wherein said cells retain metabolic activity for at least 3 days in vitro.

24. The sample of claim 23, wherein said cells retain metabolic activity for at least 4 days in vitro.

25. The sample of claim 24, wherein said cells retain metabolic activity for at least 6 days in vitro.

26. The sample of claim 25, wherein said cells retain metabolic activity for at least 10 days in vitro.

* * * * *